United States Patent
Szpilman et al.

(10) Patent No.: US 9,475,774 B2
(45) Date of Patent: Oct. 25, 2016

(54) ALPHA-HYDROGEN SUBSTITUTED NITROXYLS AND DERIVATIVES THEREOF AS CATALYSTS

(71) Applicant: Technion Research and Development Foundation Ltd., Haifa (IL)

(72) Inventors: Alex M. Szpilman, Kiryat Tivon (IL); Michal Amar, Haifa (IL)

(73) Assignee: Technion Research and Development Foundation Ltd., Haifa (IL)

( * ) Notice: Subject to any disclaimer, the term of this patent is extended or adjusted under 35 U.S.C. 154(b) by 0 days.

(21) Appl. No.: 14/453,220

(22) Filed: Aug. 6, 2014

(65) Prior Publication Data

US 2014/0350258 A1 Nov. 27, 2014

Related U.S. Application Data

(63) Continuation of application No. PCT/IL2013/050110, filed on Feb. 5, 2013.

(60) Provisional application No. 61/595,184, filed on Feb. 6, 2012.

(51) Int. Cl.
*C07D 221/14* (2006.01)
*B01J 31/02* (2006.01)
*C07C 45/39* (2006.01)

(52) U.S. Cl.
CPC .......... *C07D 221/14* (2013.01); *B01J 31/0244* (2013.01); *C07C 45/39* (2013.01)

(58) Field of Classification Search
CPC .................................................. C07D 221/14
USPC ........................................ 546/98; 568/322
See application file for complete search history.

(56) References Cited

U.S. PATENT DOCUMENTS

| | | | |
|---|---|---|---|
| 5,821,374 | A | 10/1998 | Jenny et al. |
| 2007/0232838 | A1 | 10/2007 | Iwabuchi et al. |
| 2008/0221331 | A1 | 9/2008 | Iwabuchi et al. |
| 2009/0124806 | A1 | 5/2009 | Iwabuchi et al. |
| 2010/0311977 | A1 | 12/2010 | Hamada et al. |

FOREIGN PATENT DOCUMENTS

| | | |
|---|---|---|
| JP | 2011153076 A | 8/2011 |
| WO | 2006001387 A1 | 1/2006 |
| WO | 2006105354 A1 | 10/2006 |
| WO | 2007124543 A1 | 11/2007 |
| WO | 2008117871 A1 | 10/2008 |
| WO | 2009066735 A1 | 5/2009 |
| WO | 2009145323 A1 | 12/2009 |

OTHER PUBLICATIONS

Blinco et al., (2007) The first example of an azaphenalene profluorescent nitroxide. European Journal of Organic Chemistry 2007(28): 4638-4641.
Blinco et al., (2008) Experimental and theoretical studies of the redox potentials of cyclic nitroxides. J Org Chem 73 (17): 6763-71.
Dupeyre and Rassat (1978) Nitroxydes-LXXVI: Couplages a longue distance dans les nitroxydes azatricycliques. etude par rpe et rmn. conformation du groupement nitroxyde. Tetrahedron 34(10): 1501-1507. Translated abstract.
Foroughifar et al., (2010) A Straightforward and Efficient Catalyst-free One-pot Synthesis of N-Acyl-1,3-diaryl-2-azaphenalene Derivatives via Multicomponent Reactions. Chem Lett 39(3): 180-181.
Foroughifara et al., (2010) Simple and efficient procedure for the synthesis of novel 1,3-diphenyl-2-azaphenalene derivatives via one-pot multicomponent reactions. Synthetic Communications 40(12): 1812-1821.
Graetz et al., (2005) C2-Symmetric nitroxides and their potential as enantioselective oxidants. Tetrahedron: Asymmetry 16(21): 3584-3598.
JM Bobbitt, C Brückner and N Merbouh (2009) Oxoammonium- and Nitroxide-Catalyzed Oxidations of Alcohols. In: SE Denmark (Editor), Organic Reactions, vol. 74, chapter 2, pp. 103-424. John Wiley & Sons, Inc.
Momose et al., (1997) Bicyclo[3.3.1]nonanes as synthetic intermediates. Part19.1 Asymmetric cleavage of w-azabicyclo[3.n.1]alkan-3-ones at the 'fork head'. J Chem Soc, Perkin Trans 1 9: 1307-1314.
Nelsen et al., (1978) Geometry change upon electron removal from a tetraalkylhydrazine. X-ray crystallographic structures of 9,9'-bis-9-azabicyclo[3.3.1]nonane and its radical cation hexafluorophosphate. J Am Chem Soc 100(25): 7876-7882.
Ru et al., (2010) Encapsulation of epigallocatechin-3-gallate (EGCG) using oil-in-water (O/W) submicrometer emulsions stabilized by i-carrageenan and β-lactoglobulin. J Agric Food Chem 58(19): 10373-81.
Rychnovsky et al., (1996) Enantioselective oxidation of secondary alcohols using a chiral nitroxyl (N-oxoammonium salt) catalyst. J Org Chem 61(4): 1194-1195.
Shibuya et al., (2006) 2-azaadamantane N-oxyl (AZADO) and 1-Me-AZADO: highly efficient organocatalysts for oxidation of alcohols. J Am Chem Soc 128(26): 8412-3.
Shibuya et al., (2008) Oxidative rearrangement of tertiary allylic alcohols employing oxoammonium salts. J Org Chem 73(12): 4750-4752.
Shibuya et al., (2008) TEMPO/NaIO4-SiO2: a catalytic oxidative rearrangement of tertiary allylic alcohols to β-substituted a,β-unsaturated ketones. Org Lett 10(21): 4715-4718.
Shibuya et al., (2009) An expeditious entry to 9-azabicyclo[3.3.1]nonane N-oxyl (ABNO): another highly active organocatalyst for oxidation of alcohols. J Org Chem 74(12): 4619-4622.
Tomizawa et al., (2009) Highly enantioselective organocatalytic oxidative kinetic resolution of secondary alcohols using chirally modified AZADOs. Org Lett 11(8): 1829-1831.

*Primary Examiner* — Rita Desai
(74) *Attorney, Agent, or Firm* — Roach Brown McCarthy & Gruber, P.C.; Kevin D. McCarthy

(57) ABSTRACT

Novel alpha-hydrogen substituted nitroxyl compounds and their corresponding oxidized (oxoammonium cations) and reduced (hydroxylamine) forms, and the use of such compounds, inter alia, for oxidation of primary and secondary alcohols to aldehydes and ketones, respectively; resolution of racemic alcohols; desymmetrization of meso-alcohol; as radicals and spin trapping reagents; and as polymerization agents. Processes for preparing the novel nitroxyl/oxoammonium/hydroxylamine compounds from the corresponding amines, and certain novel amine derivatives and their uses. The compounds and amine precursors are useful as ligands for transition metals and as organocatalysts in e.g., aldol reactions.

11 Claims, 7 Drawing Sheets

ALPHA-HYDROGEN SUBSTITUTED NITROXYLS AND DERIVATIVES THEREOF AS CATALYSTS

FIELD OF THE INVENTION

The present invention relates to novel alpha-hydrogen substituted nitroxyl compounds and their corresponding oxidized (oxoammonium cations) and reduced (hydroxylamine) forms, and to the use of such compounds, inter alia, for (1) oxidation of primary and secondary alcohols to aldehydes and ketones, respectively; (2) resolution of racemic alcohols; (3) desymmetrization of meso-alcohol; (4) as radicals and spin trapping reagents; and (5) as polymerization agents. The present invention further relates to processes for preparing the novel nitroxyl/oxoammonium/hydroxylamine compounds from the corresponding amines, and to certain novel amine derivatives and their uses. The compounds of the invention as well as the amine precursors are also useful as ligands for transition metals and as organocatalysts in e.g., aldol reactions.

BACKGROUND OF THE INVENTION

The synthesis of aldehydes and ketones are ubiquitous processes in industrial and academic preparation of organic compounds (drugs, fragrances, food additives etc). Current methods require stoichiometric metal oxidants or are catalyzed by expensive and potentially toxic transition metals. In addition, the oxidative resolution of chiral racemic or meso compounds is of great interest due to the role of enantio-pure alcohols as synthetic precursors and active ingredients. A serious limitation of these methods is that heavy metal containing reagents are used, leading to undesirable toxic waste which must either be deposited or undergo costly treatment. The search for more environmentally friendly methods of preparing aldehydes, ketones and of resolving alcohols is of great importance.

One known solution is the use of THE achiral nitroxyl compound 2,2,6,6-tetramethylpiperidine N-oxyl (TEMPO) (FIG. 1, compound (2)) as an organic catalyst in combination with a stoichiometric oxidant such as household bleach. TEMPO is considered to be a low environmental burden type organic oxidation catalyst as compared with heavy metals. PCT International Patent Application WO 2006/105354 discloses a process for selective oxidation of a primary alcohol of a triterpenoid to the corresponding aldehyde, using TEMPO derivatives. U.S. Pat. No. 5,821,374 (corresponding to EP 775684) discloses a process for the oxidation of alcohols using TEMPO derivatives. Shibuya, M. et al. *J. Org. Chem.* 2008, 73, 4750-4752 discloses a process for the oxidative rearrangement of tertiary allylic alcohols using TEMPO-based oxoammonium salts. Shibuya, M. et al. *Org. Lett.* 2008, 10(21), 4715-4718 discloses a process for catalytic oxidative rearrangement of tertiary allylic alcohols to β-substituted α,β-unsaturated ketones using a TEMPO/NaIO$_4$—SiO$_2$ catalyst. However, TEMPO derivatives are relatively unreactive towards secondary alcohols (Shibuya, M. et al. *J. Org. Chem.* 2009, 74, 4619-4622). This is due to the nitroxyl being flanked by sterically demanding methyl groups. Furthermore, TEMPO has a stability problem and tends to decompose (Scheme 1). In addition, TEMPO is not chiral. Most known chiral nitroxyl compounds share the sterically demanding design and reactivity profile of TEMPO.

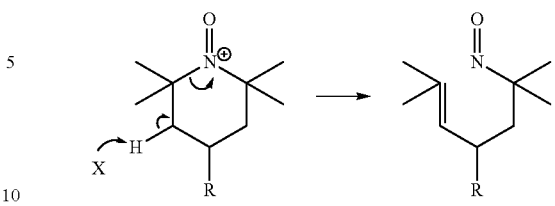

Scheme 1

One solution would be to introduce a small group (a hydrogen) on the carbon next to the nitroxyl group. However such compounds are inherently unstable, since upon oxidation tautomerization occurs leading to the nitrone which is no longer catalytically active (Scheme 2). Indeed, a recent review (J. M. Bobbitt and C. Bruckner, *Organic Reactions* vol. 74, Chapter 2) discloses: "These nitroxides are prepared by oxidation of secondary amines that contain no hydrogen on the alpha-carbon. If the amines carry alpha-hydrogens the oxidation products are nitrones, not free radical nitroxides."

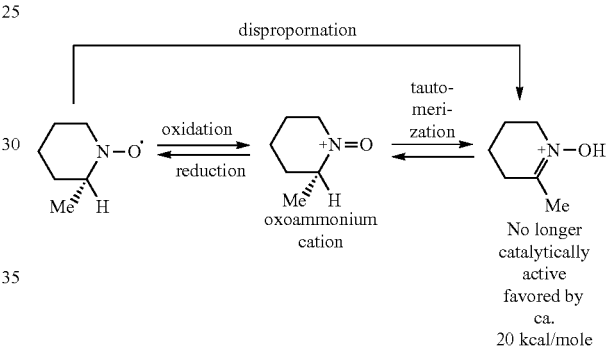

Scheme 2

One class of compounds, the bicyclic small ring compounds such as 2-azadamantan-N-oxyl (AZADO) and the related 1-methyl AZADO (Me-AZADO) (FIG. 1), offers stability to nitroxyl compounds comprising alpha-hydrogens. The stability results from the inability to form double bond containing nitrones to a bridge head atom (an example of Bredt's rule). Dupeyre, R. M. et al., *Tetrahedron*, 1978, 34, 1501-1507 discloses AZADO and its derivatives, and their characterization. Shibuya, M. et al. (i) *J. Org. Chem.* 2009, 74, 4619-4622; (ii) *J. Am. Chem. Soc.* 2006, 128, 8412-8413; and (iii) US Patent Application No. 2007/0232838 (corresponding to EP 1775296) describe the use of AZADO and Me-AZADO as organocatalysts for oxidation of primary and secondary alcohols. US Patent Application No. 2009/0124806 discloses a process for preparing a carboxylic acid from a primary alcohol, using an alkali metal chlorite as a co-oxidizing agent and an oxoammonium salt based pm AZADO and its derivatives. US Patent Application No. 2010/0311977 discloses a method for producing AZADO derivatives of formula (1) by cyclizing a compound of formula (2). The non-racemic members of this family have a very narrow scope in kinetic resolutions of racemic alcohols. In addition, the preparation of AZADO-based compounds is cumbersome and based on expensive starting materials.

Tomizawa, M. et al. *Organic Letters*, 2009, Vol. 11(8), 1829-1831 discloses chirally modified AZADO compounds and their use in resolving racemic secondary alcohols.

Graetz, B. et al., *Tetrahedron: Asymmetry*, 2005, 16, 3584-3598 discloses C2-symmetric nitroxides and their use as enantioselective oxidants of alcohols.

9-azabicyclo[3.3.1]nonane N-oxyl (ABNO, FIG. 1), is a bicyclic type nitroxyl radical structurally homologous to AZADO. The utility of ABNO as a radical trapping agent, a radical generator and a spin labeling agent has been previously reported by Nelsen, S. F. et al., *J. Am. Chem. Soc.*, 1978, 100, 7876 and Momose, T. et al., *J. Chem. Soc., Perkin Trans.*, 1, 1997, 1307. US Patent Application No. 2008/0221331 describes the use of ABNO as an alcohol oxidation catalyst. Shibuya et al., *J. Org. Chem.* 2009 describes a process for preparing ABNO and its utility as an alcohol oxidizing agent. PCT International Patent Application Nos. WO 2009/145323 (corresponding to US 2011/153076) and WO 2008/117871 describe methods of oxidizing alcohols with ABNO derivatives. These compounds suffer from the same disadvantages as AZADO-based compounds.

Blinco, J. P., Bottle, S. E. et al. *Eur. J. Org. Chem.*, 2007, 4638-4641 discloses an azaphenalene-based fused aromatic nitroxide TMAO [1,1,3,3-tetramethyl-2,3-dihydro-2-azaphenalen-2-yloxyl], and its use as a fluorescent agent. A later publication from the same authors (*J. Org. Chem.* 2008, 73, 6763-6771) describes cyclic nitroxides from four different structural classes (pyrrolidine, piperidine, isoindoline and azaphenanlene) and studies on their redox potentials. PCT International Application No. WO 2007/124543 discloses fused aromatic nitroxide compounds and their use as pro-fluorescent agents. Rychnovsky, S. D. et al., *J. Org. Chem.*, 1996, 61, 1194-1195 discloses enantioselective oxidation of secondary alcohols using a chiral nitroxyl (N-oxoammonium salt) catalyst. All of the compounds disclosed in the aforementioned publications contain alkyl, aryl, arylalkyl or heteroalkyl substituents at the alpha-positions adjacent to the nitroxyl moiety.

Given the widespread importance of aldehydes, ketones and optically active alcohols in the chemical and pharmaceutical fields, efficient reagents and synthetic methods that avoid the shortcomings of prior art processes are highly desirable.

SUMMARY OF THE INVENTION

The present invention relates to the design and preparation of a new class of alpha-hydrogen substituted nitroxyl compounds and related oxoammonium and hydroxylamine derivatives, collectively represented by the structure of formula I.

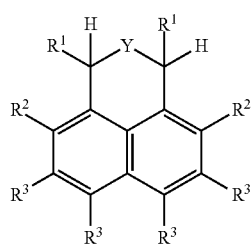

I including enantiomers, disasteromers, optically active, meso and racemic forms thereof, and salts thereof, wherein Y is

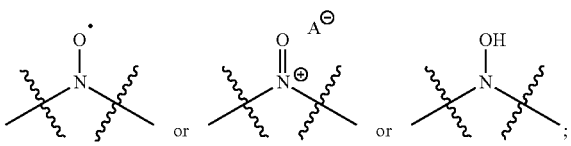

A is an anion;

$R^1$ and $R^2$, which may be the same or different from each other, are each independently at each occurrence an unsubstituted or substituted alkyl, an unsubstituted or substituted cycloalkyl, or an unsubstituted or substituted aryl; and $R^3$ is independently at each occurrence H, halo, alkyl, haloalkyl, alkenyl, alkynyl, cycloalkyl, aryl, alkylaryl, heterocyclyl, heteroaryl, hydroxy, alkoxy, aryloxy, cycloalkyloxy, heterocyclyloxy, heteroaryloxy, formyl, amino, alkylamino, dialkylamino, arylamino, diarylamino, alkylarylamino, cycloalkylamino, heterocyclylamino, heteroarylamino, amido, alkylamido, dialkylamido, arylamido, diarylamido, alkylarylamido, cycloalkylamido, heterocyclylamido, heteroarylamido, cyano, nitro, carboxyl, carboxyalkyl, carboxyaryl, acyl, —S(=O)$R^a$, —S(=O)$_2R^a$—C(=O)$R^a$ or —C(=O)O$R^a$, wherein $R^a$ is independently at each occurrence alkyl, alkenyl, alkynyl, cycloalkyl, aryl, alkylaryl, heterocyclyl or heteroaryl; wherein each of the alkyl, alkenyl, alkynyl, cycloalkyl, aryl, alkylaryl, heterocyclyl or heteroaryl may be unsubstituted or substituted.

In contrast to prior art nitroxyl compounds containing alpha hydrogens, that are unstable and tend to decompose to the catalytically inactive nitrones, it has now been discovered that the presence of the $R^2$ group in the novel compounds of the invention lends stability to the otherwise unstable hydride flanked nitroxyl function. Without wishing to be bound by any particular mechanism or theory, it is contemplated that the stability results from the development of unfavorable steric strain (allylic strain) between the $R^1$ and $R^2$ groups during decomposition to nitrones. This inhibits the decomposition process (Scheme 3). Thus, on the one hand the catalysts contain hydrogens at the positions next to the reactive center, thereby making them less sterically hindered and more reactive, and on the other hand the $R^2$ moiety acts as a steric barrier to prevent decomposition to nitrones. These properties together give rise to excellent nitroxyl-based catalysts and their related oxidized (oxoammonium cations) and reduced (hydroxylamine) forms, that are stable to decomposition on one hand and active catalysts on the other, and that can be used in a variety of reactions as described herein.

Scheme 3

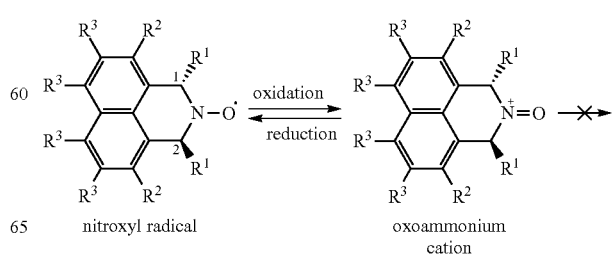

nitroxyl radical      oxoammonium cation

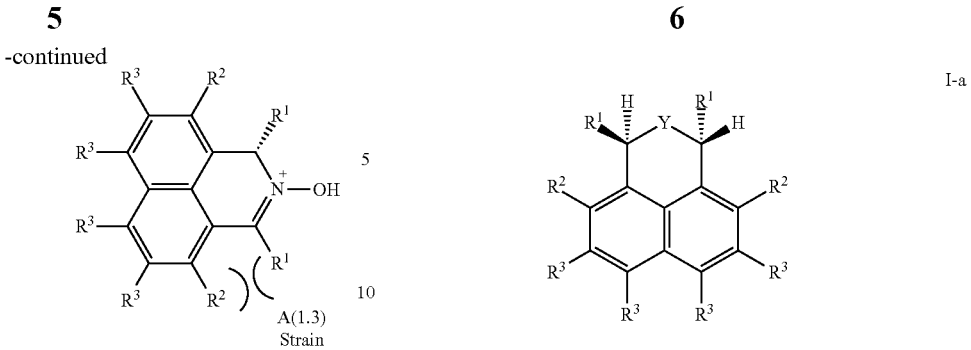

The present invention further relates to new synthetic methods for preparing the novel nitroxyl/hydroxyamine/oxoammonium catalysts that are both efficient and allow for the flexible preparation of a plethora of derivatives. The compounds catalyze oxidation of alcohols rapidly and efficiently. The compounds can be prepared in an enantiopure form and may therefore be used as a catalysts in asymmetric kinetic resolution of racemic as well as desymmetrization of meso alcohols. One possible model for the stereoselectivity of the novel catalysts is based on steric interactions between the R groups of the alcohol substrate and the substituents of the catalyst, as illustrated in FIG. 2.

The compounds of the invention are the first of the benzo-isoquinoline type to incorporate hydrogens next to the reactive center rather than alkyls. This makes the compounds inherently more reactive than known catalysts. Moreover, being organic compounds, they are environmentally friendly. Chemical waste from an industrial process based on organic catalysts may be burnt leaving no toxic byproducts behind in contrast to organometallic catalysts that leave a heavy-metal residue. The present catalysts may be used in conjunction with stoichiometric oxidants such as household bleach and trichloroisocyanuric acid (TCCA) that form environmentally friendly by-products (sodium chloride, water and urea type compounds respectively). The inventive preparation of these compounds allows easy tailoring of the nitroxyl compound for specific uses.

Compounds of formula I encompass nitroxyl derivatives (Formula II), their oxidized oxoammonium cations (Formula III) and reduced hydroxylamines (Formula IV). The structures of formulae II, III and IV are provided herein below. Each possibility represents a separate embodiment of the present invention.

The present invention further encompass enantiomers, disasteromers, optically active, meso and racemic forms of the compounds of formula I, II, III or IV. The compounds may be in racemic, optically enriched or optically pure form, with each possibility representing a separate embodiment of the presence invention. For reactions involving resolution of alcohols or desymmetization of meso-alcohols, non-racemic compounds are used.

Preferred compounds for use in the processes of the present invention are compounds represented by the structure of formula I-a, including enantiomers, racemic, optically enriched or optically pure forms thereof. For non-chiral reactions such as oxidation of alcohols, the racemate of formula I-a may be used. For chiral reactions such as resolution of racemic alcohols or desymmetrization of meso alcohols, optically active derivatives of formula I-a are used.

Compounds of formula I-a encompass nitroxyl derivatives (Formula II-a), their oxidized oxoammonium cations (Formula III-a) and reduced hydroxylamines (Formula IV-a), and enantiomers, racemic, optically enriched or optically pure forms thereof. The structures of compounds II-a, III-a and IV-a are provided hereinbelow. Each possibility represents a separate embodiment of the present invention.

A currently preferred catalyst is a compound represented by the structure of formula 1 (nitroxyl), and its corresponding oxidized (oxoammonium) and reduced (hydroxylamine) forms. Another currently preferred catalyst is a compound represented by the structure of formula 2 (nitroxyl), and its corresponding oxidized (oxoammonium) and reduced (hydroxylamine) forms. Another currently preferred catalyst is a compound represented by the structure of formula 3 (nitroxyl), and its corresponding oxidized (oxoammonium) and reduced (hydroxylamine) forms. Another currently preferred catalyst is a compound represented by the structure of formula 4 (nitroxyl), and its corresponding oxidized (oxoammonium) and reduced (hydroxylamine) forms. Another currently preferred catalyst is a compound represented by the structure of formula 5 (nitroxyl), and its corresponding oxidized (oxoammonium) and reduced (hydroxylamine) forms. Another currently preferred catalyst is a compound represented by the structure of formula 6 (nitroxyl), and its corresponding oxidized (oxoammonium) and reduced (hydroxylamine) forms. Another currently preferred catalyst is a compound represented by the structure of formula 7 (nitroxyl), and its corresponding oxidized (oxoammonium) and reduced (hydroxylamine) forms. The structures of these compounds are shown in the detailed description hereinbelow. Each possibility represents a separate embodiment of the present invention.

In some embodiments, the compounds of the invention are symmetric compounds, in which case each $R^1$ is the same at each occurrence and/or each $R^2$ is the same at each occurrence and/or each $R^3$ is the same at each occurrence, with each possibility representing a separate embodiment of the present invention.

In other embodiments, the compounds of the invention are asymmetric compounds, in which case each $R^1$ is different at each occurrence and/or each $R^2$ is different at each occurrence and/or each $R^3$ is different at each occurrence, with each possibility representing a separate embodiment of the present invention.

In other embodiments, $R^1$ and $R^2$ are the same. In other embodiments, $R^1$ and $R^2$ are different. Each possibility represents a separate embodiment of the present invention.

The present invention further provides various processes which utilize compounds of the present invention as catalysts.

Thus in one embodiment, the present invention relates to a process for oxidizing a primary alcohol to the corresponding aldehyde by reacting the primary alcohol with a compound of any of formulae I, I-a, II, II-a, III, III-a, IV, or IV-a, optionally in the presence of a co-oxidizing agent.

In another embodiment, the present invention relates to a process for oxidizing a secondary alcohol to the corresponding ketone by reacting the secondary alcohol with a compound of any of formulae I, I-a, II, II-a, III, III-a, IV, or IV-a, optionally in the presence of a co-oxidizing agent.

In another embodiment, the present invention relates to a process for resolution of a racemic alcohol comprising at least one stereocenter, by reacting the racemic alcohol with a compound of any of formulae I, I-a, II, II-a, III, III-a, IV, or IV-a, wherein the compound is in a non-racemic form, and optionally further in the presence of a co-oxidizing agent.

In another embodiment, the present invention relates to a process for desymmetrization of a meso-alcohol, by reacting the alcohol with a compound of any of formulae I, I-a, II, II-a, III, III-a, IV, or IV-a, wherein the compound of formula I is in a non-racemic form (i.e., it is optically active) and optionally further in the presence of a co-oxidizing agent.

In one embodiment, a nitroxyl derivative of formula II or II-a, or a hydroxylamine derivative of formula IV or IV-a is used, and the processes of the present invention are further conducted in the presence of a co-oxidizing agent. Preferably, the process is conducted in the presence of catalytic (sub-stoichiometric) amounts of the nitroxyl or hydroxylamine derivative, and a stoichiometric amount of the co-oxidizing agent, relative to the amount of alcohol. Each possibility represents a separate embodiment of the present invention.

The nature of the co-oxidizing agent is not particularly limiting. In one embodiment, the co-oxidizing agent is an organic N-chloro compounds, non-limiting examples of which include trichloroisocyanuric acid (TCCA), 1,3-dichloro-5,5-dimethylhydantoin (DCH), N-chloro-4-toluenesulphonamide and salts thereof (Chloramine T), N-chlorobenzene-sulphonamide and salts thereof (Chloramine B), bleach (NaClO), a hypervalent iodine such as iodobenzene dichloride or iodobenzene diacetate, and combinations thereof.

In another embodiment, an oxoammonium derivative of formula III or III-a is used. In this case, no co-oxidizing agent is necessary for the processes of the invention, and the process utilizes stoichiometric amount of the oxoammonium derivative relative to the amount of alcohol.

Further uses of the novel catalysts of the present invention include as spin trapping reagents, as ligands for transition metals, as organocatalysts for an aldol reaction, or as polymerization agents.

Also encompassed by the present invention are processes for preparing the novel catalysts of the present invention and certain intermediates formed or used in these processes. Thus, in one embodiment, the present invention relates to a process for the preparation of a compound represented by the structure of formula I as described above. The process comprises the steps of oxidizing an amine derivative represented by the structure of formula V in the presence of an oxidizing agent

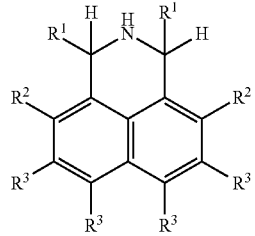

wherein $R^1$, $R^2$ and $R^3$ are as defined above for formula I.

In some embodiments, the oxidizing agent is selected from the group consisting of peroxides (e.g., hydrogen peroxide ($H_2O_2$) and m-chloro-p-benzoic acid (mCPBA)), bleach (NaOCl), $Na_2WO_4 \cdot 2H_2O$, oxygen ($O_2$), ozone ($O_3$), and the like. Each possibility represents a separate embodiment of the present invention.

The amine precursors are also novel compounds and represent a separate embodiment of the present invention. Thus, in one embodiment, the present invention relates to an amine compound represented by the structure of formula V wherein $R^1$, $R^2$ and $R^3$ are as defined above for formula I.

In other embodiments, the present invention relates to an amine compound represented by the structure of formula V-a

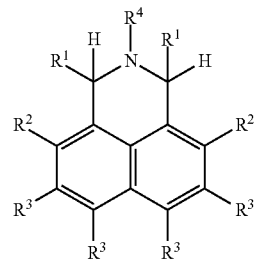

wherein $R^1$ is an unsubstituted or substituted alkyl, an unsubstituted or substituted cycloalkyl, or an unsubstituted or substituted aryl;

$R^2$ and $R^4$ are each H, an unsubstituted or substituted alkyl, an unsubstituted or substituted cycloalkyl, or an unsubstituted or substituted aryl; and $R^3$ is independently at each occurrence H, halo, alkyl, haloalkyl, alkenyl, alkynyl, cycloalkyl, aryl, alkylaryl, heterocyclyl, heteroaryl, hydroxy, alkoxy, aryloxy, cycloalkyloxy, heterocyclyloxy, heteroaryloxy, formyl, amino, alkylamino, dialkylamino, arylamino, diarylamino, alkylarylamino, cycloalkylamino, heterocyclylamino, heteroarylamino, amido, alkylamido, dialkylamido, arylamido, diarylamido, alkylarylamido, cycloalkylamido, heterocyclylamido, heteroarylamido, cyano, nitro, carboxyl, carboxyalkyl, carboxyaryl, acyl, —S(=O)$R^a$, —S(=O)$_2R^a$—C(=O)$R^a$ or —C(=O)O$R^a$, wherein $R^a$ is independently at each occurrence alkyl, alkenyl, alkynyl, cycloalkyl, aryl, alkylaryl, heterocyclyl or heteroaryl; wherein each of the alkyl, alkenyl, alkynyl, cycloalkyl, aryl, alkylaryl, heterocyclyl or heteroaryl may be unsubstituted or substituted.

The amine precursors of formula V or V-a can be prepared in accordance with a process comprising the steps of:

(a) reacting an aldehyde, an amine and a 2,7-naphthol derivative to obtain an intermediate represented by the structure of formula VI;

(b) converting the hydroxyl groups in the compound of formula VI into a reactive derivative thereof so as to generate a compound of formula VII wherein OR' is a leaving group;

(c) reacting the compound of formula VII with a reagent that introduces the group $R^2$ so as to generate a compound of formula VIII:

(d) removing the protecting group P so as to generate a compound of formula V or a compound of formula V-a wherein $R^4$ is H; and (e) optionally, introducing the group $R^4$;

wherein $R^1$, $R^2$, $R^3$, $R^4$ are as defined above for formula V or V-a, and P is an amino protecting group

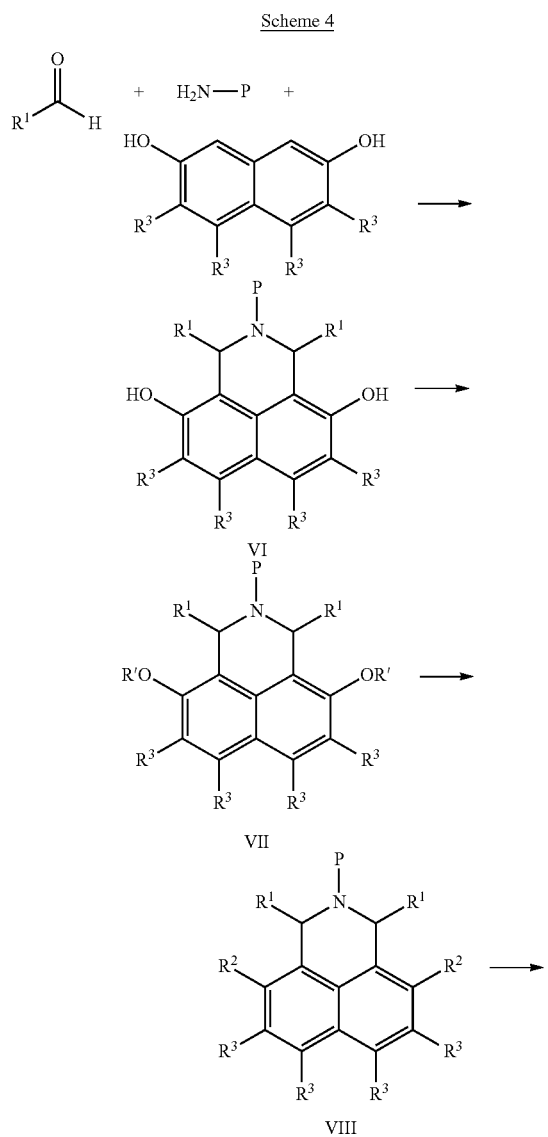

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
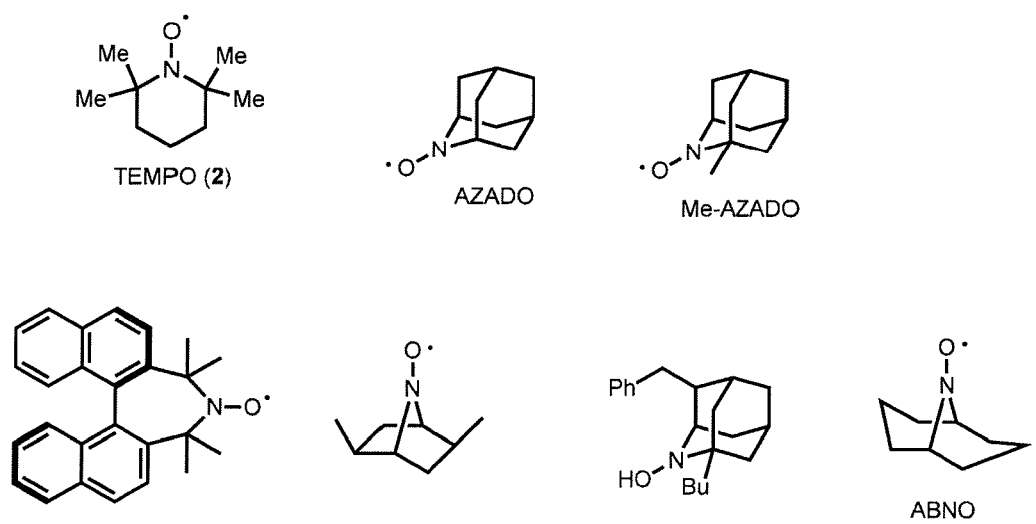
FIG. 1 shows the structures of nitroxyl radicals known in the literature.
Figure 2:
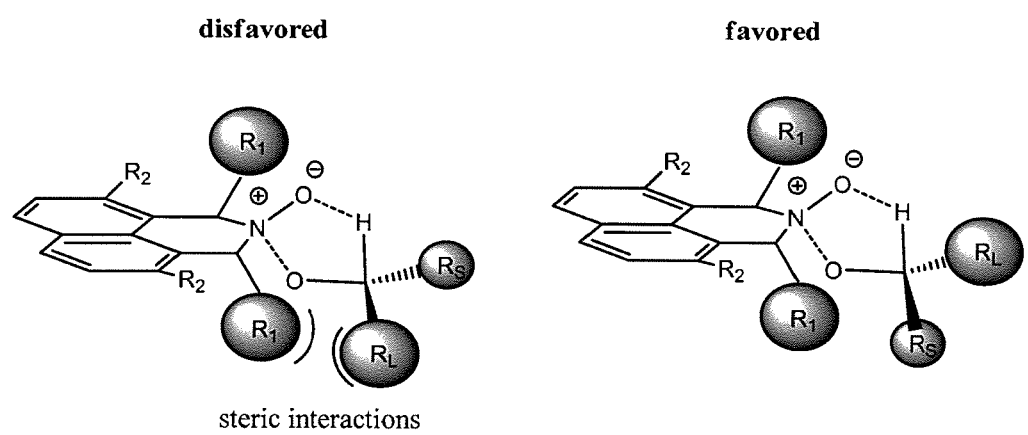
FIG. 2 shows a model for stereoselectivity of the chiral catalysts of the present invention.

The present invention relates to novel alpha-hydrogen substituted nitroxyl compounds and their corresponding oxidized (oxoammonium cations) and reduced (hydroxylamine) forms, and to the use of such compounds, inter alia, for (1) oxidation of primary and secondary alcohols to aldehydes and ketones, respectively; (2) resolution of racemic alcohols; (3) desymmetrization of meso-alcohol; (4) as radicals and spin trapping reagents; and (5) as polymerization agents. The present invention further relates to processes for preparing the novel nitroxyl/oxoammonium/hydroxylamine compounds from the corresponding amines, and to certain novel amine derivatives and their uses. The compounds of the invention as well as the amine precursors are also useful as ligands for transition metals and as organocatalysts in e.g., aldol reactions.

Chemical Definitions

An "alkyl" group as used herein refers to any saturated aliphatic hydrocarbon, including straight and branched-chain. In one embodiment, the alkyl group has 1-12 carbons designated here as $C_1$-$C_{12}$-alkyl. In another embodiment, the alkyl group has 1-6 carbons designated here as $C_1$-$C_6$-alkyl. In another embodiment, the alkyl group has 1-4 carbons designated here as $C_1$-$C_4$-alkyl. Examples of alkyl groups include, but are not limited to, methyl, ethyl, n-propyl, isopropyl, n-butyl, iso-butyl, sec-butyl, tert-butyl, amyl, tert-amyl, and hexyl. Similarly, the term "$C_1$ to $C_{12}$ alkylene" denotes a bivalent radical of 1 to 12 carbons.

The alkyl group can be unsubstituted, or substituted with one or more substituents selected from the group consisting of halogen, alkyl (e.g., C1-C6 alkyl), hydroxy, alkoxy (e.g., C1-C6 alkoxy), aryloxy, alkylaryloxy, heteroaryloxy, oxo, cycloalkyl, phenyl, heteroaryl, heterocyclyl, naphthyl, amino, alkylamino, arylamino, heteroarylamino, dialkylamino, diarylamino, alkylarylamino, alkylheteroarylamino, arylheteroarylamino, acyl, acyloxy, nitro, carboxy, carbamoyl, carboxamide, cyano, sulfonyl, sulfonylamino, sulfinyl, sulfinylamino, alkylsulfonyl or arylsulfonyl groups. By way of illustration, an "alkoxyalkyl" is an alkyl that is substituted with an alkoxy group. Each possibility represents a separate embodiment of the present invention.

An "alkenyl" group as used herein refers to an unsaturated hydrocarbon containing at least one double bond. The alkenyl group generally includes 2 to 12 carbon atoms (a $C_2$-$C_{12}$ alkenyl). Examples of alkenyl groups include, but are not limited to, vinyl, allyl, butenyl and the like. Similarly, the term "$C_2$ to $C_{12}$ alkenylene" denotes a bivalent radical of 2 to 12 carbons. The alkenyl group can be unsubstituted or substituted with any one or more of the substituents defined above for alkyl.

An "alkynyl" group as used herein refers to any unsaturated hydrocarbon containing at least one triple bond. The alkynyl group generally includes 2 to 12 carbon atoms (a $C_2$-$C_{12}$ alkynyl). Examples of alkynyl groups include, but are not limited to, ethynyl, propynyl and the like. Similarly, the term "$C_2$ to $C_{12}$ alkynylene" denotes a bivalent radical of 2 to 12 carbons. The alkynyl group can be unsubstituted or substituted with any one or more of the substituents defined above for alkyl.

A "cycloalkyl" group as used herein refers to a "$C_3$ to $C_8$ cycloalkyl" and denotes any unsaturated monocyclic, bicyclic or polycyclic group. Nonlimiting examples of cycloalkyl groups are cyclopropyl, cyclobutyl, cyclopentyl, cyclohexyl or cycloheptyl. The cycloalkyl group can be unsubstituted or substituted with any one or more of the substituents defined above for alkyl. Similarly, the term "cycloalkylene" means a bivalent radical where the cycloalkyl radical is bonded at two positions connecting together two separate additional groups.

An "aryl" group as used herein refers to an aromatic ring system containing from 6-14 ring carbon atoms. The aryl ring can be a monocyclic, bicyclic, tricyclic and the like. Non-limiting examples of aryl groups are phenyl, naphthyl including 1-naphthyl and 2-naphthyl, and the like. The aryl group can be unsubstituted or substituted through available carbon atoms with one or more groups defined hereinabove for alkyl. One currently preferred aryl group is phenyl. Another currently preferred aryl group is naphthyl.

An "alkylaryl" group as used herein refers to an alkyl group as defined herein bonded to an aryl group as defined herein. An example of an alkylaryl group is a benzyl group. The alkylaryl group can be unsubstituted or substituted through available carbon atoms with one or more groups defined hereinabove for alkyl.

The term "heteroaryl" used herein alone or as part of another group denotes a heteroaromatic system containing at least one heteroatom ring atom selected from nitrogen, sulfur and oxygen. The heteroaryl generally contains 5 or more ring atoms. The heteroaryl group can be monocyclic, bicyclic, tricyclic and the like. Also included in this expression are the benzoheteroaromatic rings. If nitrogen is a ring atom, the present invention also contemplates the N-oxides of the nitrogen containing heteroaryls. Nonlimiting examples of heteroaryls include thienyl, benzothienyl, 1-naphthothienyl, thianthrenyl, furyl, benzofuryl, pyrrolyl, imidazolyl, pyrazolyl, pyridyl, pyrazinyl, pyrimidinyl, pyridazinyl, indolyl, isoindolyl, indazolyl, purinyl, isoquinolyl, quinolyl, naphthyridinyl, quinoxalinyl, quinazolinyl, cinnolinyl, pteridinyl, carbolinyl, thiazolyl, oxazolyl, isothiazolyl, isoxazolyl and the like. The heteroaryl group can be unsubtituted or substituted through available atoms with one or more groups defined hereinabove for alkyl.

The term "heterocyclic ring" or "heterocyclyl" used herein alone or as part of another group denotes a five-membered to eight-membered rings that have 1 to 4 heteroatoms, such as oxygen, sulfur and/or nitrogen. These rings can be saturated, fully unsaturated or partially unsaturated. Non-limiting examples of heterocyclic rings include piperidinyl, piperidinyl, pyrrolidinyl pyrrolinyl, pyrazolinyl, pyrazolidinyl, piperidinyl, morpholinyl, thiomorpholinyl, pyranyl, thiopyranyl, piperazinyl, indolinyl, dihydrofuranyl, tetrahydrofuranyl, dihydrothiophenyl, tetrahydrothiophenyl, dihydropyranyl, tetrahydropyranyl, and the like. The heterocyclyl group can be unsubstituted or substituted through available atoms with one or more groups defined hereinabove for alkyl.

The term "halo" as used herein refers to a halogen (e.g., F, Cl, Br, I). The term "cyano" refers to a —CN group. The term "nitro" refers to a —$NO_2$ group.

The term "hydroxy" as used herein refers to an OH group. The term "alkyloxy" or "alkoxy", used herein interchangeably, refers to an O-alkyl group. The term "aryloxy" refers to an O-aryl group. The term "cycloalkyloxy" as used herein refers to an O-cycloalkyl group. The term "heterocyclyloxy" as used herein refers to an O-heterocyclyl group. The term "heteroaryloxy" as used herein refers to an O-heteroaryl group. Each of these groups may be unbustituted or may be substituted by any one or more of the substituents defined above for alkyl.

The term "amino" as used herein refers to an $NH_2$ group. The amino group may be substituted by one or more of an alkyl, aryl, cycloalkyl, heterocyclyl or heteroaryl groups as those groups are defined above.

The term "amido" as used herein refers to an —C(=O)$NH_2$ group. The amido group may be substituted by one or more of an alkyl, aryl, cycloalkyl, heterocyclyl or heteroaryl groups as those groups are defined above.

The term "formyl" as used herein refers to a —C(=O)H group. The term "carboxy" as used herein refers to a —C(=O)OH group. The term "carboxyalkyl" as used herein refers to a carboxy group bonded to an alkyl group. The term "carboxyaryl" as used herein refers to a carboxy group bonded to an aryl group.

All stereoisomers, optical and geometrical isomers of the compounds of the instant invention are contemplated, either in admixture or in pure or substantially pure form. The compounds of the present invention can have asymmetric centers at any of the sp3 hybridized carbon atoms. Consequently, the compounds can exist in enantiomeric or diastereomeric forms or in mixtures thereof. The present invention contemplates the use of any racemates (i.e. mixtures containing equal amounts of each enantiomer), enantiomerically enriched mixtures (i.e., mixtures enriched for one enantiomer, for example about 10-90% enantiomeric excess (ee) of each enantiomer), substantially pure enantiomers (greater than about 90% ee), or diastereomers, or any mixtures thereof. The chiral centers can be designated as R or S or R,S or d,D, l,L or d,l, D,L. Meso compounds (i.e., compounds containing pro-stereogenic centers) are also covered.

The term "amino protecting group" as used herein refers to a readily cleavable group bonded to an amino group. The nature of the amino protecting group is not critical so long as the derivatized amino group is stable. Non-limiting examples of amino-protecting groups include t-butoxycarbonyl, benzyloxycarbonyl, acetyl, phenylcarbonyl, or a silyl group, which can be substituted with alkyl (trialkylsilyl), with an aryl (triarylsilyl) or a combination thereof (e.g., dialkylphenylsilyl), e.g., trimethylsilyl (TMS) or t-butyldimethyl silyl (TBDMS). Other suitable amino-protecting agents and amino-protecting groups, as well as methods of protection and deprotection, have been described in, e.g., T. W. Greene and P. G. M. Wuts, Protective Groups in Organic Synthesis, $2^{nd}$ Ed., John Wiley and Sons (1991) and A. J. Pearson and W. R. Roush, Activating Agents and Protecting Groups, John Wiley and Sons (1999), each of which is incorporated herein by reference.

Compounds

The present invention relates to the design and preparation of a new class of alpha-hydrogen substituted nitroxyl compounds and related oxoammonium and hydroxylamine derivatives, collectively represented by the structure of formula I.

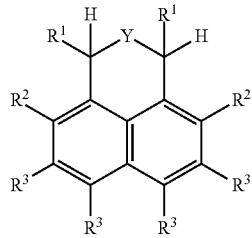
I including enantiomers, disasteromers, optically active, meso and racemic forms thereof, and salts thereof, wherein
Y is

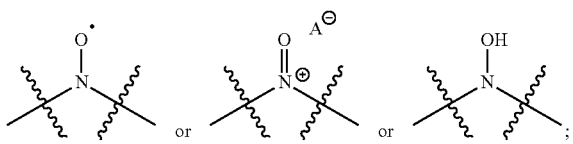
or           or         ;

A is an anion;

$R^1$ and $R^2$, which may be the same or different from each other, are each independently at each occurrence an unsubstituted or substituted alkyl, an unsubstituted or substituted cycloalkyl, or an unsubstituted or substituted aryl; and $R^3$ is independently at each occurrence H, halo, alkyl, haloalkyl, alkenyl, alkynyl, cycloalkyl, aryl, alkylaryl, heterocyclyl, heteroaryl, hydroxy, alkoxy, aryloxy, cycloalkyloxy, heterocyclyloxy, heteroaryloxy, formyl, amino, alkylamino, dialkylamino, arylamino, diarylamino, alkylarylamino, cycloalkylamino, heterocyclylamino, heteroarylamino, amido, alkylamido, dialkylamido, arylamido, diarylamido, alkylarylamido, cycloalkylamido, heterocyclylamido, heteroarylamido, cyano, nitro, carboxyl, carboxyalkyl, carboxyaryl, acyl, —S(=O)$R^a$, —S(=O)$_2R^a$—C(=O)$R^a$ or —C(=O)O$R^a$, wherein $R^a$ is independently at each occurrence alkyl, alkenyl, alkynyl, cycloalkyl, aryl, alkylaryl, heterocyclyl or heteroaryl; wherein each of the alkyl, alkenyl, alkynyl, cycloalkyl, aryl, alkylaryl, heterocyclyl or heteroaryl may be unsubstituted or substituted.

Compounds of formula I encompass nitroxyl derivatives (Formula II), their oxidized oxoammonium cations (Formula III) and reduced hydroxylamines (Formula IV):

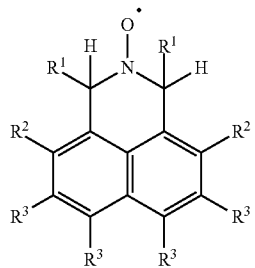
II

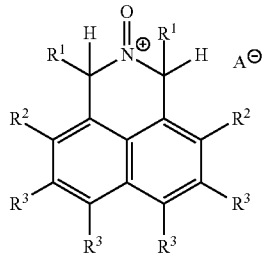
III

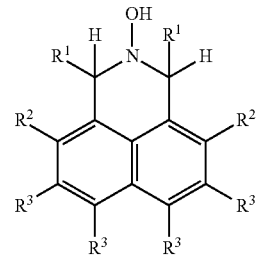
IV

The present invention further encompass enantiomers, disasteromers, optically active, meso and racemic forms of the compounds of formula I, II, III or IV. The compounds may be in racemic, optically enriched or optically pure form, with each possibility representing a separate embodiment of the presence invention. For reactions involving resolution of alcohols or desymmetization of meso-alcohols, non-racemic (i.e., optically active) compounds are used.

In some preferred embodiments, the compound of formula (I) is represented by the structure of formula I-a, and enantiomers, racemic, optically enriched or optically pure forms thereof.

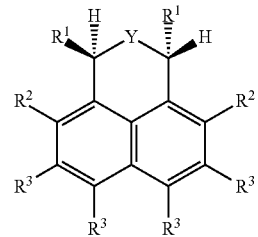
I-a

Compounds of formula I-a encompass nitroxyl derivatives (Formula II-a), their oxidized oxoammonium cations (Formula III-a) and reduced hydroxylamines (Formula IV-a), and enantiomers, racemic, optically enriched or optically pure forms thereof.

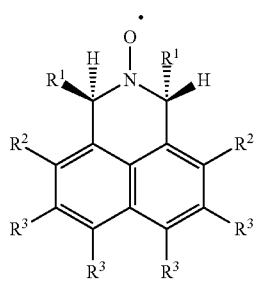
II-a

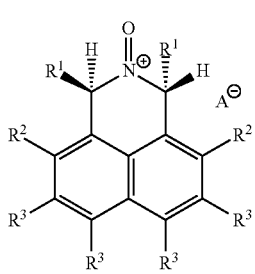

III-a

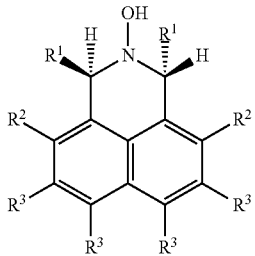

IV-a

The present invention further encompass enantiomers, disasteromers, optically active and racemic forms of the compounds of formula I-a. The compounds may be in racemic, optically enriched or optically pure form, with each possibility representing a separate embodiment of the presence invention. For reactions involving resolution of alcohols or desymmetization of meso-alcohols, non-racemic (i.e., optically active) compounds are used. For non-chiral reactions such as oxidation of alcohols, the racemic forms are preferably used.

As contemplated herein, the present invention encompasses the R,R and S,S enantiomers of the compounds of formula II-a, III-a and IV-a, each in optically pure form, optically enriched form, or racemic form.

In some preferred embodiments, $R^1$ in Formula I-IV or Ia-IVa is an unsubstituted or substituted aryl. In one preferred embodiment, $R^1$ is phenyl. In another preferred embodiment, $R^1$ is a phenyl substituted by one or more substituents, wherein each substituent is preferably a $C_1$-$C_6$ alkyl, a $C_1$-$C_6$ alkoxy, or a halogen. Currently preferred $R^1$ groups are selected from the group consisting of phenyl, 4-chlorophenyl, naphthyl, anisyl (methoxyphenyl, preferably 4-methoxyphenyl) and mesityl (1,3,5-trimethylphenyl). In other preferred embodiments, $R^1$ in Formula I-IV or Ia-IVa is naphthyl. Each possibility represents a separate embodiment of the present invention.

In other preferred embodiments, $R^1$ in Formula I-IV or Ia-IVa is an unsubstituted or substituted alkyl, preferably a $C_1$-$C_6$ alkyl, such as methyl, ethyl, propyl, isopropyl, n-butyl, isobutyl, sec-butyl and t-butyl, preferably $R^1$ is isopropyl. Each possibility represents a separate embodiment of the present invention.

In some preferred embodiments, $R^2$ in Formula I-IV or Ia-IVa is an unsubstituted or substituted $C_1$-$C_6$ alkyl. In other preferred embodiments, $R^2$ in Formula I-IV or Ia-IVa is an unsubstituted or substituted $C_3$-$C_8$ cycloalkyl. Preferably, $R^2$ is methyl or cyclohexyl. Each possibility represents a separate embodiment of the present invention.

In one preferred embodiments, $R^3$ in Formula I-IV or Ia-IVa is hydrogen.

One preferred catalyst is represented by the structure of formula 1. Other preferred catalysts include the oxoammonium and hydroxylamine counterparts of said catalyst. The compound of formula 1 is preferably racemic, but can also be provided in the form of either enantiomer or any mixture thereof.

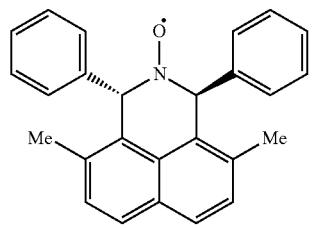

1

Another preferred catalyst is represented by the structure of formula 2. Other preferred catalysts include the oxoammonium and hydroxylamine counterparts of said catalyst. The compound of formula 2 is preferably racemic, but can also be provided in the form of either enantiomer or any mixture thereof.

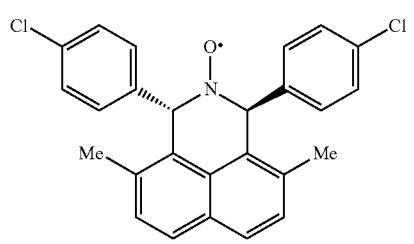

2

Another preferred catalyst is represented by the structure of formula 3. Other preferred catalysts include the oxoammonium and hydroxylamine counterparts of said catalyst. The compound of formula 3 is preferably racemic, but can also be provided in the form of either enantiomer or any mixture thereof.

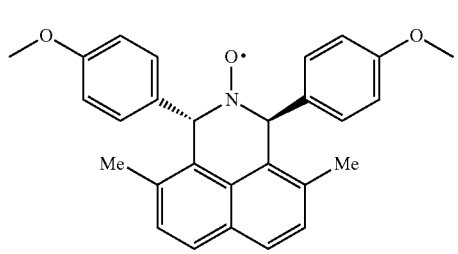

3

Another preferred catalyst is represented by the structure of formula 4. Other preferred catalysts include the oxoammonium and hydroxylamine counterparts of said catalyst. The compound of formula 4 is preferably racemic, but can also be provided in the form of either enantiomer or any mixture thereof.

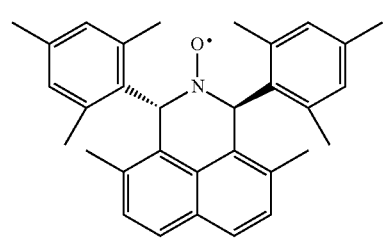

4

Another preferred catalyst is represented by the structure of formula 5. Other preferred catalysts include the oxoammonium and hydroxylamine counterparts of said catalyst. The compound of formula 5 is preferably racemic, but can also be provided in the form of either enantiomer or any mixture thereof.

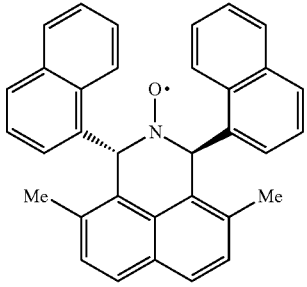

5

Another preferred catalyst is represented by the structure of formula 6. Other preferred catalysts include the oxoammonium and hydroxylamine counterparts of said catalyst. The compound of formula 6 is preferably racemic, but can also be provided in the form of either enantiomer or any mixture thereof.

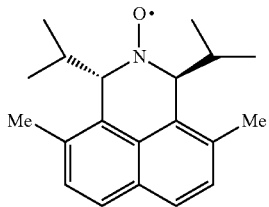

6

Another preferred catalyst is represented by the structure of formula 7, demonstrating an example of an asymmetric catalyst. Other preferred catalysts include the oxoammonium and hydroxylamine counterparts of said catalyst. The compound of formula 7 is preferably racemic, but can also be provided in the form of either enantiomer or any mixture thereof.

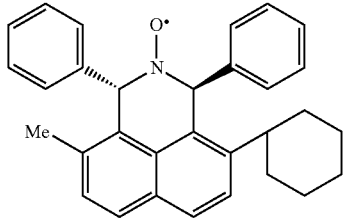

7

The term "anion" as used herein refers to any moiety or group bearing a negative charge, for example as a counterion to the oxoammonium cations of the present invention. Examples of anionic moieties include, but are not limited to halogen (e.g., F, Cl, Br, I), OCOR', OCOCF$_3$, OSO$_2$R', OSO$_2$CF$_3$, BE$_4$, PF$_6$, SbF$_6$, BR'$_4$, ClO$_4$, AlCl$_4$, CN, OH, OR' or NR'$_2$ wherein R' is selected from alkyl, cycloalkyl, aryl, alkylaryl, heterocyclyl and heteroaryl, wherein each of the alkyl, cycloalkyl, aryl, alkylaryl, heterocyclyl and heteroaryl is as defined above.

One or more of the compounds of the invention, may be present as a salt. The term "salt" encompasses both basic and acidic addition salts, including but not limited to phosphate, dihydrogen phosphate, hydrogen phosphate and phosphonate salts, and include salts formed with organic and inorganic anions and cations. Furthermore, the term includes salts that form by standard acid-base reactions of basic groups and organic or inorganic acids. Such acids include hydrochloric, hydrofluoric, hydrobromic, trifluoroacetic, sulfuric, phosphoric, acetic, succinic, citric, lactic, maleic, fumaric, cholic, pamoic, mucic, D-camphoric, phthalic, tartaric, salicyclic, methanesulfonic, benzenesulfonic, p-toluenesulfonic, sorbic, picric, benzoic, cinnamic, and like acids. The salts of the compounds may preferably include acceptable or usable nontoxic or low toxic inorganic acid and organic acid salts and acceptable or usable nontoxic or low toxic inorganic base and organic base salts. Examples of such salts include salts with halogen atom-derived anions (e.g. Cl$^-$, Br$^-$, I$^-$, etc.), formates, acetates, propionates, fumarates, oxalates, maleates, succinates, tartrates, trifluoroacetates; alkali metal salts such as sodium salts and potassium salts, alkaline earth metal salts such as calcium salts and magnesium salts, aluminum salts, ammonium salts, methylamine salts, ethylamine salts, trimethylamine salts, triethylamine salts, aniline salts, pyridine salts, piperidine salts, picoline salts, ethanolamine salts, diethanolamine salts, triethanolamine salts, dicyclohexylamine salts, N,N'-dibenzylethylenediamine salts, tetrafluoroborate salts, hexafluorophosphate salts, etc.

Preferably, the compounds of the invention are symmetric compounds, in which case R$^1$ is the same at each occurrence and/or R$^2$ is the same at each occurrence and/or R$^3$ is the same at each occurrence, with each possibility representing a separate embodiment of the present invention. However, asymmetrical catalysts are also encompassed by the present invention.

Novel Uses

The present invention further provides various processes which utilize the novel nitroxyl catalysts of the present invention as catalysts.

Thus in one embodiment, the present invention relates to a process for oxidizing a primary alcohol to the corresponding aldehyde by reacting the primary alcohol with a compound of any of formulae I, I-a, II, II-a, III, III-a, IV, or IV-a, optionally in the presence of a co-oxidizing agent. In another embodiment, the present invention relates to a process for oxidizing a secondary alcohol to the corresponding ketone by reacting the secondary alcohol with a compound of any of formulae I, I-a, II, II-a, III, III-a, IV, or IV-a, optionally in the presence of a co-oxidizing agent.

These reactions are illustrated in Scheme 5:

Scheme 5

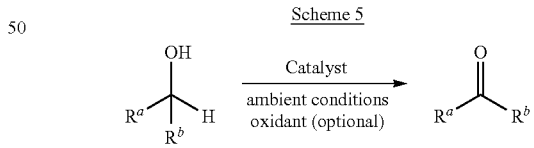

R$^a$, R$^b$ = alkyl, aryl, cycloalkyl, H, etc.

The nature of the alcohol being oxidized is not particularly limiting. In Scheme 5, R$^a$ and R$^b$ can be the same or they can be different from each other, with each possibility representing a separate embodiment of the present invention. A variety of primary and secondary alcohols can be used in the process of the invention. Each of R$^a$ and R$^b$ as described above can, independently of the other, be H, or an unsubstituted or substituted alkyl, aryl, heteroaryl, heterocyclyl, alkylaryl, cycloalkyl, alkenyl, alkynyl, and the like, or the two R group can be joined to form a cyclic moiety. In some embodiments, the primary alcohol is selected from the group consisting of methanol, ethanol, 1-propanol, 1-butanol, 1-pentanol, 1-hexanol, 2-methoxyethanol, 2-methyl-1-butanol, benzyl alcohol, and the like. In other embodiments, the secondary alcohol is selected from the group consisting of isopropanol, isobutanol, sec-butanol, 2-pentanol, 3-pentanol, 2-hexanol, 3-hexanol, menthol, cyclopentanol, cyclohexanol, cycloheptanol, borneol, decahydronaphthalen-1-ol, decahydronaphthalen-2-ol, 1-phenylpropan-1-ol, 1-phenylethanol, 2-methyl-1-phenylpropan-1-ol, 2,2-dimethyl-1-phenylpropan-1-ol, 2-hydroxy-1,2-diphenylethanone, 2,2-dimethyloctan-3-ol, and the like. Any substituted derivatives of these alcohols may also be used as substrates or starting materials in the processes of the present invention. Each possibility represents a separate embodiment of the present invention.

In another embodiment, the present invention relates to a process for resolution of a racemic alcohol comprising at least one stereocenter, by reacting the racemic alcohol with a compound of any of formulae I, I-a, II, II-a, III, III-a, IV, or IV-a, wherein the compound is in a non-racemic form, and optionally further in the presence of a co-oxidizing agent. This process is described in Scheme 6:

Scheme 6

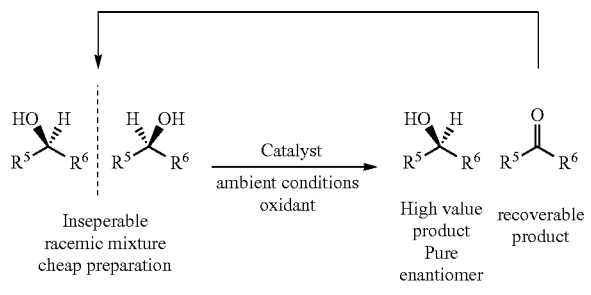

Inseperable racemic mixture cheap preparation

High value product Pure enantiomer recoverable product

Easy to separate

The nature of the alcohol being resolved is not particularly limiting. A variety of alcohols can be used in the process of the invention, so long as they contain at least one chiral center (stereocenter). $R^5$ and $R^6$ and Scheme 6 are different from each other and are each independently an unsubstituted or substituted alkyl, aryl, heteroaryl, heterocyclyl, alkylaryl, cycloalkyl, alkenyl, alkynyl, and the like, or they can together form a cyclic moiety. Each possibility represents a separate embodiment of the present invention.

In another embodiment, the present invention relates to a process for desymmetrization of a meso-alcohol, by reacting the alcohol with a compound of any of formulae I, I-a, II, II-a, III, III-a, IV, or IV-a, wherein the compound of formula (I) is in a non-racemic form and optionally further in the presence of a co-oxidizing agent. This process is described in Scheme 7A:

Scheme 7A

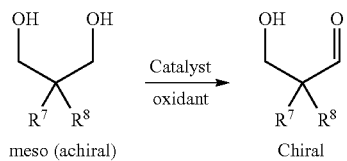

meso (achiral)        Chiral wherein $R^7$ and $R^8$ and Scheme 7A are different from each other and are each independently H, or an unsubstituted or substituted alkyl, aryl, heteroaryl, heterocyclyl, alkylaryl, cycloalkyl, alkenyl, alkynyl, and the like, or they can together form a cyclic moiety. Each possibility represents a separate embodiment of the present invention. An example of such a process is described in Scheme 7B.

Scheme 7B

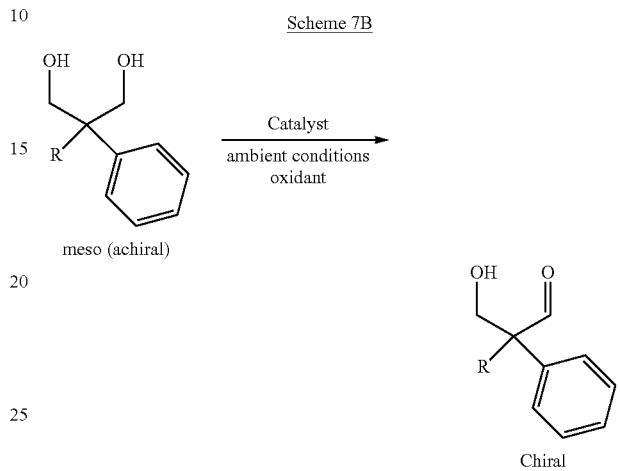

meso (achiral)

Chiral wherein R is H, or an unsubstituted or substituted alkyl, aryl, heteroaryl, heterocyclyl, alkylaryl, cycloalkyl, alkenyl, alkynyl, and the like. Each possibility represents a separate embodiment of the present invention. Again, the nature of the alcohol is not particularly limiting, and any meso-alcohol can be used in the process of the present invention.

For any of the above-referenced reactions, the catalysts of the present invention may be added to a mixture containing at least one or more reactant starting materials. Alternatively, the reactant starting material(s) may be added to a solvent containing at least the compound of formula I, or a derivative thereof of any of formulae I, I-a, II, II-a, III, III-a, IV or IV-a.

The proportion of the compound of formula I, or a derivative thereof, to the starting material alcohol is not particularly limited to, so long as the desired level of catalytic activity can be obtained, but the compound of formula I, can be used, for example, in a mole ratio of about 1:100,000 to 1:1, preferably about 1:10,000 to 2:3, more preferably 1:1,000 to 1:10. When a nitroxyl radical or a hydroxylamine derivative is used, the catalyst is preferably provided in substoichiometric amounts relative to the amount of alcohol (in a molar ratio of about 1:1,000,000 to less than about 1:1 catalyst relative to the alcohol). When an oxoammonium derivative is used, the catalyst is preferably provided in stoichiometric amounts (i.e., about 1:1 or even a slight excess of the catalyst) relative to the amount of alcohol. The catalyst of the invention may be added to the reaction mixture in the form of a mixture of the compound of formula I (which can be a nitroxyl, an oxoammonium or a hydroxylamine derivative) with such an oxidizing agent as an aqueous sodium hypochlorite solution.

In one embodiment, a nitroxyl derivative of formula II or II-a is used, and the processes of the present invention are further conducted in the presence of a co-oxidizing agent. Preferably, the process is conducted in the presence of catalytic (sub-stoichiometric) amounts of the nitroxyl derivative of formula II or II-a, and a stoichiometric amount of the oxidizing agent, relative to the amount of alcohol. Each possibility represents a separate embodiment of the present invention.

In another embodiment, a hydroxylamine derivative of formula IV or IV-a is used, and the processes of the present invention are further conducted in the presence of a co-oxidizing agent. Preferably, the process is conducted in the presence of catalytic (sub-stoichiometric) amounts of the hydroxylamine derivative of formula IV or IV-a, and a stoichiometric amount of the oxidizing agent, relative to the amount of alcohol. Each possibility represents a separate embodiment of the present invention.

The term "stoichiometric amount" means about an equimolar amount (1:1) of the catalyst or co-oxidizing agent. relative to the amount of the substrate alcohol. The term stoichiometric amount also encompasses a slight excess (e.g., about 5%, about 10% or about 15%) of the catalyst or the co-oxidizing agent or both, relative to the amount of substrate alcohol.

The nature of the co-oxidizing agent is not particularly limiting. In one embodiment, the co-oxidizing agent is an organic N-chloro compound, non-limiting examples of which include trichloroisocyanuric acid (TCCA), 1,3-dichloro-5,5-dimethylhydantoin (DCH), N-chloro-4-toluenesulphonamide and salts thereof (Chloramine T), N-chlorobenzene-sulphonamide and salts thereof (Chloramine B), bleach (NaClO), a hypervalent iodine such as iodobenzene dichloride or iodobenzene diacetate, and combinations thereof. Examples of co-oxidants are described in Scheme 8:

Scheme 8

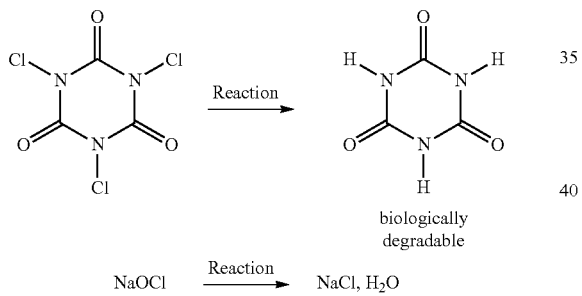

biologically degradable

In another embodiment, an oxoammonium derivative of formula III or III-a is used. In this case, no co-oxidizing agent is necessary for the processes of the invention, and the process utilizes about stoichiometric amount of the oxoammonium derivative relative to the amount of alcohol.

Further uses of the novel catalysts of the present invention include as spin trapping reagents, or as ligands for transition metals, or as organocatalysts for an aldol reaction, or as polymerization agents.

Synthetic Methods and Novel Intermediates

As contemplated herein, the applicants have developed a novel synthesis of a new class of alpha-hydrogen substituted nitroxyl compounds and amines, as well as their corresponding oxoammonium and hydroxylamine derivatives. The nitroxyl and hydroxylamine compounds may be used in sub-stoichiometric amounts as catalysts for the oxidation of alcohols, in the presence of co-oxidants. The oxoammonium compounds may be used in stoichiometric amounts as catalysts for the oxidation of alcohols.

The synthesis of the novel catalysts of the present invention utilizes a variant of a recently published method (N. Foroughifar et al. (i) Chemistry Letters 2010. 39(3), 180, and (ii) Synthetic Communications, 2010, 40, 1812-1821), the contents of each of which are incorporated herein. According to this process, which is illustrated in Scheme 4 hereinabove, 2,7-napthol reacts with and imine generated in situ from an aldehyde (which provides $R^1$) and a primary amine. The resulting adduct is treated in situ to form the backbone of the molecule in high yield (up to 95%) and diastereoselectivity (up to about 17:1). The two phenol groups are converted into triflate esters which serve as the reactive locus for introducing the $R^2$ substituent.

In one embodiment, the $R^2$ substituent is introduced via a coupling reaction (exemplified below for introduction of a methyl group via a Stille-coupling). Next the protecting group of the amine is cleaved and the resulting secondary amine oxidized to the racemic nitroxyl using any of several methods. The nitroxyl compounds are characterized by ESR/EPR spectra as demonstrated herein.

Alternatively, prior to coupling the amine is resolved at any of the stages preceding oxidation. After oxidation the enantiopure nitroxyl compound is formed.

Thus, in one embodiment, the present invention relates to a process for the preparation of a compound represented by the structure of formula I as described above. The process comprises the steps of oxidizing an amine derivative represented by the structure of formula V in the presence of an oxidizing agent

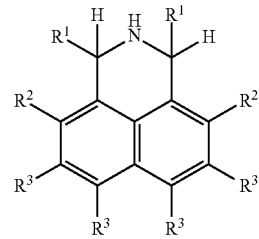

V wherein $R^1$, $R^2$ and $R^3$ are as defined above for formula I.

In some embodiments, the oxidizing agent is selected from the group consisting of peroxides (e.g., hydrogen peroxide ($H_2O_2$) and m-chloro-p-benzoic acid (mCPBA)), bleach (NaOCl), $Na_2WO_4.2H_2O$, oxygen ($O_2$), ozone ($O_3$), and the like. Each possibility represents a separate embodiment of the present invention.

The amine precursors are also novel compounds and represent a separate embodiment of the present invention. Thus, in one embodiment, the present invention relates to an amine compound represented by the structure of formula V wherein $R^1$, $R^2$ and $R^3$ are as defined above for formula I.

In other embodiments, the present invention relates to an amine compound represented by the structure of formula V-a

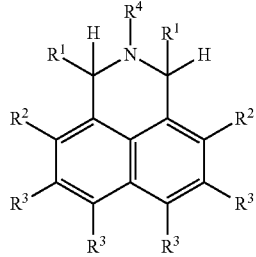

V-a wherein

R¹ is an unsubstituted or substituted alkyl, an unsubstituted or substituted cycloalkyl, or an unsubstituted or substituted aryl;

R² and R⁴ are each H, an unsubstituted or substituted alkyl, an unsubstituted or substituted cycloalkyl, or an unsubstituted or substituted aryl; and R³ is independently at each occurrence H, halo, alkyl, haloalkyl, alkenyl, alkynyl, cycloalkyl, aryl, alkylaryl, heterocyclyl, heteroaryl, hydroxy, alkoxy, aryloxy, cycloalkyloxy, heterocyclyloxy, heteroaryloxy, formyl, amino, alkylamino, dialkylamino, arylamino, diarylamino, alkylarylamino, cycloalkylamino, heterocyclylamino, heteroarylamino, amido, alkylamido, dialkylamido, arylamido, diarylamido, alkylarylamido, cycloalkylamido, heterocyclylamido, heteroarylamido, cyano, nitro, carboxyl, carboxyalkyl, carboxyaryl, acyl, —S(=O)R$^a$, —S(=O)$_2$R$^a$—C(=O)R$^a$ or —C(=O)OR$^a$, wherein R$^a$ is independently at each occurrence alkyl, alkenyl, alkynyl, cycloalkyl, aryl, alkylaryl, heterocyclyl or heteroaryl; wherein each of the alkyl, alkenyl, alkynyl, cycloalkyl, aryl, alkylaryl, heterocyclyl or heteroaryl may be unsubstituted or substituted.

The amine precursors can be prepared in accordance with a process comprising the steps of (see, Scheme 4):

(a) reacting an aldehyde, an amine and a 2,7-naphthol derivative to obtain an intermediate represented by the structure of formula VI;

(b) converting the hydroxyl groups in the compound of formula VI into a reactive derivative thereof so as to generate a compound of formula VII wherein OR' is a leaving group;

(c) reacting the compound of formula VII with a reagent that introduces the group R² so as to generate a compound of formula VIII:

(d) removing the protecting group P so as to generate a compound of formula V or a compound of formula V-a wherein R⁴ is H; and (e) optionally, introducing the group R⁴;

wherein R¹, R², R³, R⁴ are as defined above for formula V or V-a, and P is an amino protecting group.

In other embodiments, the present invention further includes methods of using the amines of formula V or V-a as ligands for transition metals, or as organocatalysts for an aldol reaction.

The principles of the present invention are demonstrated by means of the following non-limiting examples.

EXAMPLES

Specific compounds which are representative of this invention were prepared as per the following examples and reaction sequences; the examples and the figures depicting the reaction sequences are offered by way of illustration, to aid in the understanding of the invention and should not be construed to limit in any way the invention set forth in the claims which follow thereafter.

The following abbreviations are used:
d=doublet
Et=ethyl
DCH=1,3-Dichloro-5,5-dimethylhydantoin;
DCE=1,2-dichloroethane;
DCM=dichloromethane;
DMB=2,4-dimethoxybenzyl
DMF=N,N-dimethylformamide;
m=multiplet;
Me=methyl
m-CPBA=meta-ChloroPerBenzoic Acid
NMR=nuclear magnetic resonance;
rt=room temperature;
t=triplet
TFA=TriFluoro-Acetic acid
TCCA tricholroisocyanuric acid.
Tf=triflate=trifluorosulfonic
TLC=Thin Layer Chromatography All compounds in the following examples are racemic unless indicated otherwise.

Example 1

Synthesis of Nitroxyl Radical (1)

A. Synthesis of the Common Nitroxyl Precursor for R¹=phenyl

Step 1: Assembly of the Tricyclic Structure

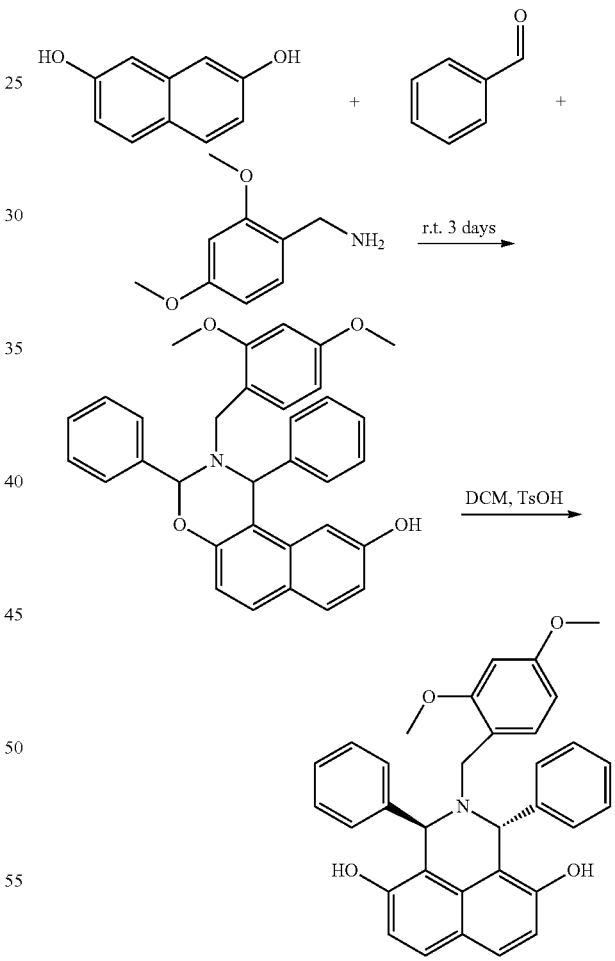

1.5 eq. of 2,4-dimethoxybenzylamine (1.56 gr, 9.36 mmol) and 6 eq. of benzaldehyde (3.97 gr, 3.8 ml, 37.44 mmol) were stirred in a round flask under nitrogen for 45 min. 1 eq. of 2,7-naphthalenediol (1 gr, 6.24 mmol) was added into the reaction mixture and the stirring was continued for 3 days. After all the naphthalenediol reacted and the monoproduct was also reacted to give the cyclic hemiacetal, 30 ml of dry DCM and 1.5 eq. of p-toluenesulfonic acid monohydrate (1.78 gr, 9.36 mmol) were added. The reaction mixture was stirred until all the cyclic hemiacetal product reacted to give the desired product. Saturated NaHCO$_3$ was added for extraction. The organic layer was dried over Na$_2$SO$_4$ and the solvent was removed under vacuum. The product was purified with flash chromatography starting with 10% ethylacetate in hexane to remove the benzaldehyde followed by 18% ethylacetate in hexane.

$^1$H NMR (400 MHz, Acetone) δ 7.94 (s, 2H), 7.55 (d, J=8.6 Hz, 2H), 7.23 (d, J=8.3 Hz, 1H), 7.11 (m, 10H), 6.85 (d, J=8.7 Hz, 2H), 6.43 (s, 1H), 6.39 (d, J=8.4 Hz, 1H), 5.31 (s, 2H), 3.71 (s, 3H), 3.68 (s, 3H), 3.58 (d, J=15.3 Hz, 1H), 3.29 (d, J=14.5 Hz, 1H).

$^{13}$C NMR (101 MHz, Acetone) δ=159.61, 158.39, 150.28, 143.01, 131.07, 129.73, 129.47, 127.28, 127.22, 126.35, 123.06, 119.49, 118.11, 115.28, 104.58, 97.86, 58.67, 54.59, 54.56, 44.91.

HRMS (ESI) m/z: calcd for C$_{33}$H$_{29}$NO$_4$, [M+1] 504.59. found 504.2148.

Step 2: Functionalization of the Hydroxyl Function as Triflate Esters

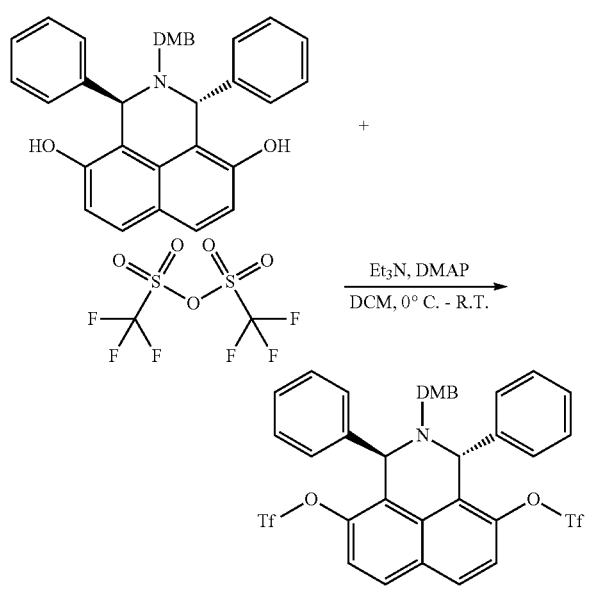

A stirred solution of 1 eq. of the cyclic diol (500 mg, 0.99 mmol) in 20 ml of dry DCM was cooled to 0° C. with an ice bath under argon. 6 eq. of Et$_3$N (602.89 mg, 0.831 ml, 5.958 mmol) and 0.1 eq. of DMAP (12.13 mg, 0.0993 mmol) were added into the stirred solution. A solution of 3 eq. of triflic anhydride (840.5 mg, 0.501 ml, 2.979 mmol) in 2 ml of dry DCM was added dropwise into the reaction mixture. After all the starting material was reacted (in about 30 min.) according to TLC (20% EtOAc in hexane) the reaction was quenched with water. The organic layer was extracted, washed with brine and dried over Na$_2$SO$_4$. The solvent was removed under vacuum. The crude product was purified by column chromatography on silica gel with elution by 10% EtOAc in hexane to give the desired bistriflate product.

$^1$H NMR (400 MHz, Acetone) δ 8.20 (d, J=9.1 Hz, 2H), 7.58 (d, J=9.1 Hz, 1H), 7.25 (m, 6H), 7.09 (m, 5H), 6.49 (d, J=2.1 Hz, 1H), 6.40 (dd, J=8.4, 2.2 Hz, 1H), 5.46 (s, 2H), 3.72 (s, 6H), 3.63 (d, J=14.6 Hz, 1H), 3.37 (d, J=14.6 Hz, 1H).

$^{13}$C NMR (101 MHz, Acetone) δ=161.09, 159.35, 144.68, 139.84, 132.25, 131.09, 130.72, 130.66, 130.45, 129.05, 128.79, 122.08, 120.93, 118.44, 117.75, 105.84, 98.88, 59.74, 55.58, 55.51, 45.46.

HRMS (ESI) m/z: calcd for C$_{35}$H$_{27}$F$_6$NO$_8$S$_2$, [M+1] 768.71. found 768.1182.

B. Preparation of Nitroxyl Catalyst R$^2$=methyl

Step 1: Introduction of the Methyl Through Cross-Coupling

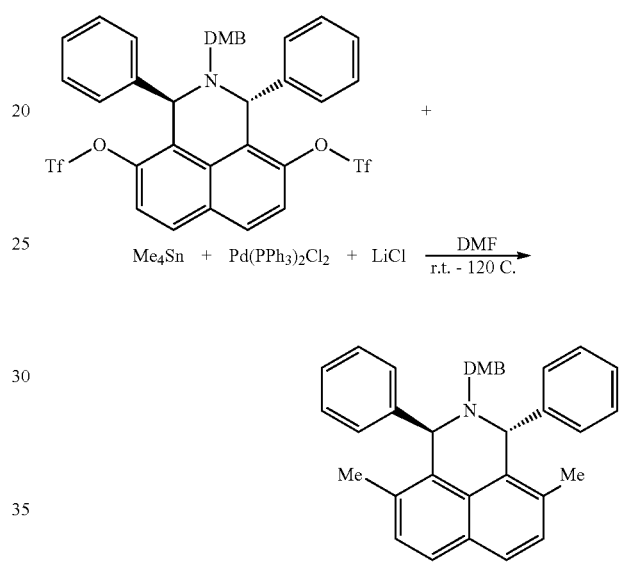

10 eq. of LiCl (110.22 mg, 2.6 mmol) were placed in a 10 ml 2 necked flask, dried with an heat gun under high vacuum and refilled with argon for 3 times. After LiCl was cooled to r.t. 2 ml of dry DMF were added, followed by 1 eq. of cyclic bistriflate (200 mg, 0.26 mmol)) and 2 eq. of Me$_4$Sn (0.072 ml, 0.52 mmol). The mixture was stirred for 15 min. then 0.1 eq. of palladium catalyst were added (18.25 mg, 0.026 mmol). The reaction mixture was heated to 125° C. and more 5 eq. of Me$_4$Sn (0.216 ml, 1.56 mmol) were added dropwise. When all the starting material was reacted (and no mono product was left also) the heating was stopped and the reaction was quenched by adding water to the reaction mixture. The product was extracted with DCM and dried over Na$_2$SO$_4$. The solvent was removed under vacuum. The crude product was purified by column chromatography on silica gel with elution by 5% EtOAc in hexane to give the desired dimethyl product.

$^1$H NMR (400 MHz, CDCl$_3$) δ 7.65 (d, J=8.3 Hz, 2H), 7.22 (d, J=8.3 Hz, 1H), 7.16 (m, 8H), 7.00 (m, 4H), 6.41 (m, 2H), 5.20 (s, 2H), 3.79 (s, 3H), 3.76 (s, 3H), 3.66 (d, J=15.0 Hz, 1H), 3.45 (d, J=15.0 Hz, 1H), 2.01 (s, 6H).

$^{13}$C NMR (101 MHz, CDCl$_3$) δ=159.37, 158.36, 141.32, 134.31, 131.30, 130.57, 130.47, 129.86, 129.37, 128.83, 127.82, 126.82, 125.98, 120.08, 104.55, 98.32, 61.30, 55.48, 55.31, 44.85, 20.68.

HRMS (ESI) m/z: calcd for C$_{35}$H$_{33}$NO$_2$, [M+1] 500.64. found 500.2598.

Step 2: Removal of the 2,3-dimethoxy Protection Group

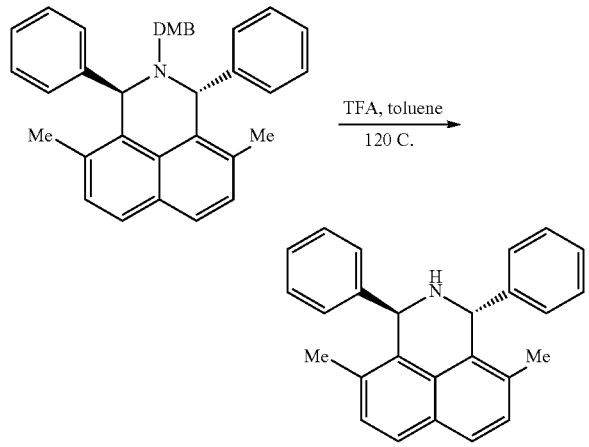

A 10 ml round flask was equipped with a condenser and a stirring bar. 350 mg (0.7 mmol) of the starting material were dissolved in 2 ml of TFA and 3 ml of toluene under nitrogen. The reaction mixture was heated to reflux and the reaction was stirred overnight. TLC (20% EtOAc in hexane) was held after mini-workup (extraction with sat. NaHCO$_3$) to see if no starting material was left. After all the starting material reacted, the reaction was cooled to r.t. and sat. NaHCO$_3$ was added during stirring. The reaction was extracted with DCM and dried over Na$_2$SO$_4$. The solvent was removed under vacuum. The crude product was purified by column chromatography on silica gel with elution by 3-5% EtOAc in hexane to give the desired deprotected amine.

$^1$H NMR (400 MHz, CDCl$_3$) δ 7.71 (d, J=8.2 Hz, 2H), 7.22 (m, 8H), 7.07 (d, J=5.6 Hz, 4H), 5.35 (s, 2H), 2.01 (s, 6H).

$^{13}$C NMR (101 MHz, CDCl$_3$) δ=143.51, 132.04, 131.27, 130.84, 129.85, 128.58, 128.46, 128.24, 127.04, 126.51, 56.99, 20.57.

HRMS (ESI) m/z: calcd for C$_{26}$H$_{23}$N, [M+1] 350.47. found 350.1868.

Step 3: Oxidation of the Amine Function to the Nitroxyl State

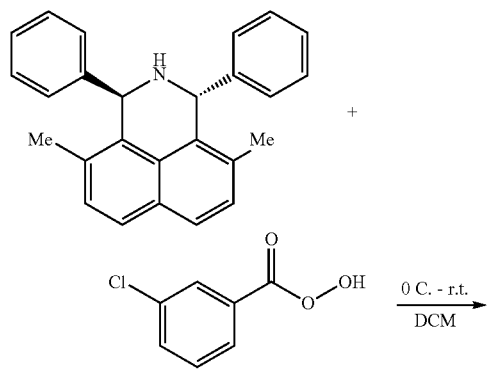

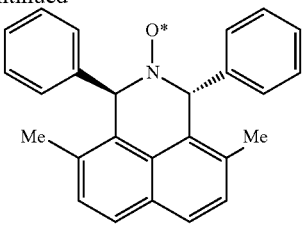

50 mg of deprotected amine (0.143 mmol) were dissolved in 2.5 ml of dry DCM and cooled to 0° C. under argon. 1.2 eq. of m-CPBA (42.4 mg, 0.172 mmol) was added and the reaction mixture was stirred at 0° C. for 10 min. This mixture can be used for catalysis with a secondary oxidant like TCCA to oxidize secondary alcohols to ketone. In order to do a kinetic resolution reaction the secondary oxidant is about 0.6 eq. parallel to about 1 eq. of the alcohol.

HRMS (ESI) m/z: calcd for C$_{26}$H$_{22}$NO, [M+1] 365.46. found 364.1705.

Figure 3:
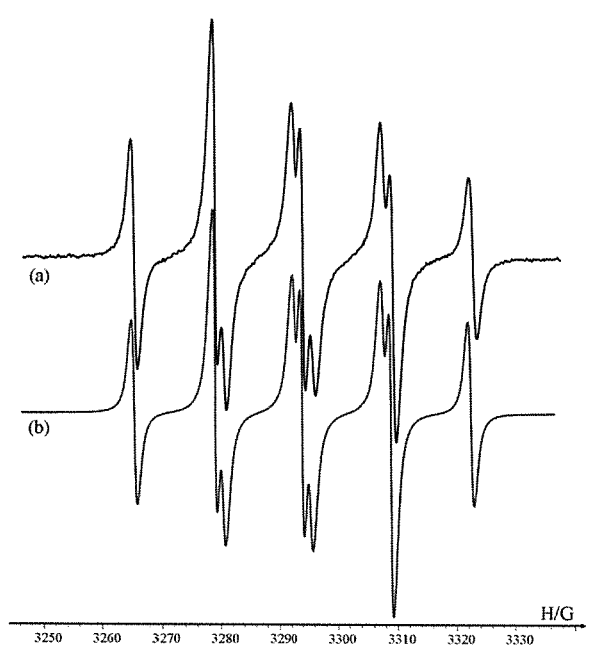
FIG. 3: ESR/EPR spectrum of nitroxyl catalyst 1 in toluene at room temperature, (b) simulated EPR spectrum.

The experimental room temperature EPR spectrum of the nitroxyl radical [1] g=2.0059 (FIG. 3a) in (toluene) characterized by interaction of unpaired electron with two protons (of cycle) [aH(2H)=13.5 G] and with atom 14N nuclei (14N has a nuclear spin of 1) [aN(14N)=15.0 G]. A computer-simulated EPR spectrum of [1] (FIG. 3b) shows full agreement with experimental data.

Figure 7:
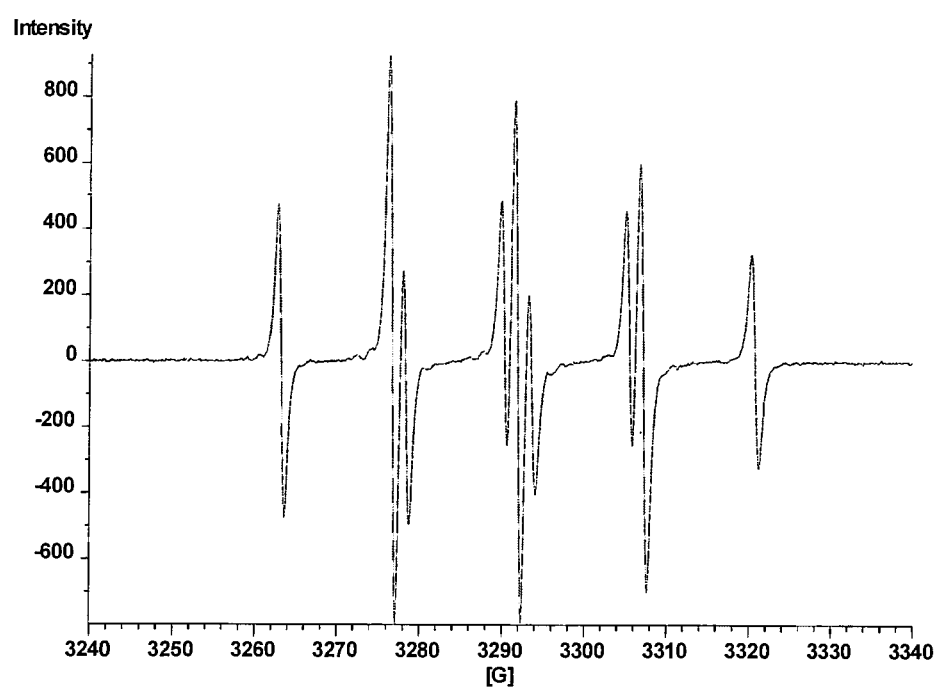
FIG. 7: ESR/EPR spectrum of nitroxyl catalyst 1 in toluene at room temperature.

FIG. 7 shows a higher resolution EPR spectrum of compound [1].

Example 2

Application of Nitroxyl R$^1$=phenyl R$^2$=methyl as Catalyst for Oxidation of Alcohols to Carbonyls: Menthol A solution of 1 eq. of TCCA (232.41 mg, 1 mmol) and 2 eq. of NaHCO$_3$ (168.02 mg, 2 mmol) in 4 ml of dry DCM was prepared in a round 10 ml flask. The mixture was stirred and cooled to 0° C. with an ice bath then 1 eq. (1 mmol) of menthol was added to the solution. Freshly made catalyst prepared as described above (0.02 eq) was added to the stirred reaction mixture. The cooling was discontinued and the reaction mixture allowed to warm to room temperature. After all the alcohol was oxidized to the desired product menthone, the reaction mixture was filtered through a piece of cotton. The solvent was removed under vacuum. The crude product was purified by column chromatography on silica gel to afford menthone 81% yield. NMR was identical to the published data.

Example 3

Application of Nitroxyl R$^1$=phenyl R$^2$=methyl as Catalyst for Oxidation of Alcohols to Carbonyls: Cyclohexanol A solution of 1 eq. of TCCA (232.41 mg, 1 mmol) and 2 eq. of NaHCO$_3$ (168.02 mg, 2 mmol) in 4 ml of dry DCM was prepared in a round 10 ml flask. The mixture was stirred and cooled to 0° C. with an ice bath then 1 eq. (1 mmol) of cyclohexanol was added to the solution. Freshly made catalyst prepared as described above (0.02 eq) was added to the stirred reaction mixture. The cooling was discontinued and the reaction mixture allowed warming to room temperature. After 1.5 hours full conversion was observed. Cyclohexanone was the only product as determined by TLC.

Example 4

Application of Nitroxyl Catalyst of Formula (I) for Oxidation of Alcohols to Carbonyls—General Procedure

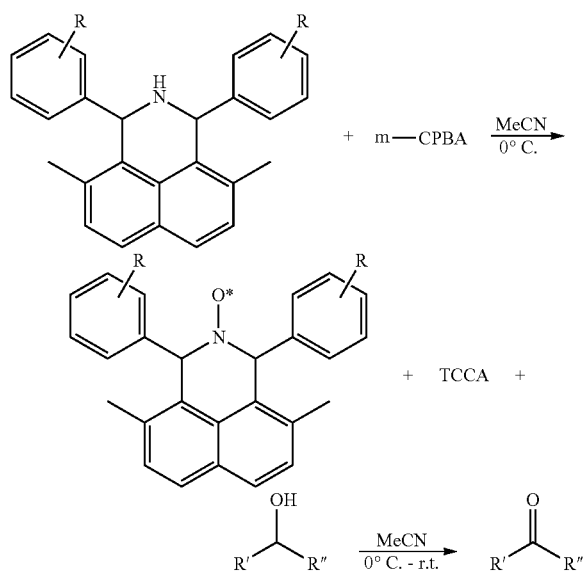

0.01 mmol of free amine were dissolved in 2.5 ml of dry MeCN and cooled to 0° C. 0.015 mmol of m-CPBA were added to the reaction mixture and the mixture was stirred for 5 min. 0.4 mmol of TCCA and 0.5 mmol of the alcohol were added into the reaction mixture and the stirring was continued until full oxidation of the alcohol shown by T.L.C. The solvent was evaporated and the product was purified by flash chromatography.

TABLE 1

Results-Alcohol Oxidation

| catalyst | Alcohol | Time | Isolated Yield | Notes |
|---|---|---|---|---|
| R = Mesityl | (structure with OH and t-Bu, phenyl) | 2.5 hr | 94% | |
| R = phenyl | menthol | 30 min | 88% | product is volatile |
| R = phenyl | borneol | 30 min | 98% | |
| R = phenyl | (benzoin structure with OH) | 5.5 hr | 96.8% | |
| R = phenyl | (structure with OH, t-Bu, butyl chain) | 10 min | 69% | product is volatile |
| R = phenyl | (decalin-OH structure) | 15 min | 100% conversion | product is volatile |

Example 5

Cyclic Amine—General Synthesis

The following amines can be used as precursors for the preparation of compounds of Formula (I), or they can be used as ligands for transition metals, or as organocatalysts for, e.g., aldol reactions.

Step A—Cyclization

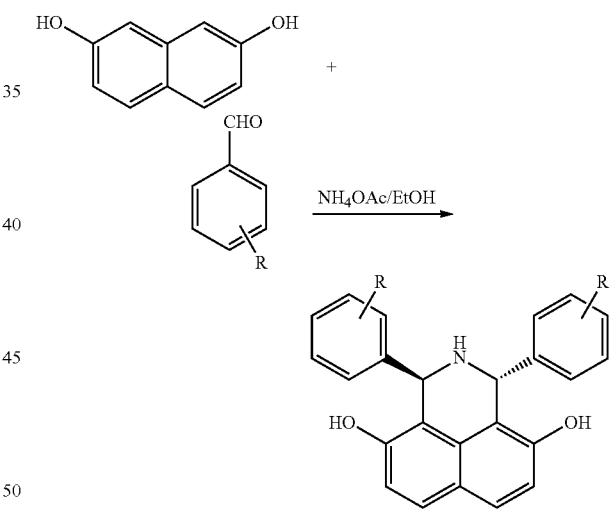

A mixture of 2,7-naphthalenediol (1 mmol), aromatic aldehyde (2.2 mmol), and ammonium acetate (1.2 mmol) in ethanol (5 ml) was stirred under reflux conditions for an appropriate time for full conversion of 2,7-naphthalenediol to the cyclic azaphenalen structure. After completion of the reaction the solvent was evaporated and saturated aqueous NaCl (20 ml) was added to the mixture, the suspension was stirred for 30 min and the precipitate filtered, washed with water and air dried. The crude product was washed with mixture of ethyl acetate/n-hexane, (20 ml, 1:4) to afford the pure product.

Step A for aliphatic aldehyde: 1 ml of a solution of 7N ammonia in methanol was added to 1.9 mmol of freshly distilled aliphatic aldehyde. The reaction mixture was stirred for 30 min. and 2,7 naphthalenediol (0.63 mmol) was added to the mixture. The reaction was stirred until full consumption of naphthalenediol (several days). The solvent was evaporated and the product was purified by column chromatography over silica gel.

Structures of Representative Intermediates:

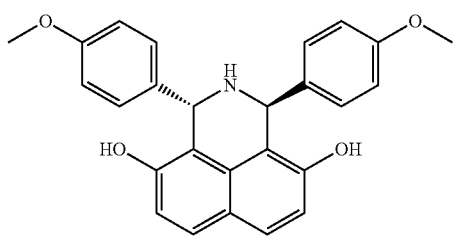

94%

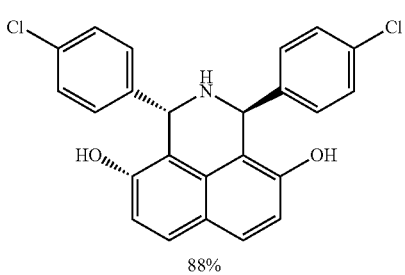

88%

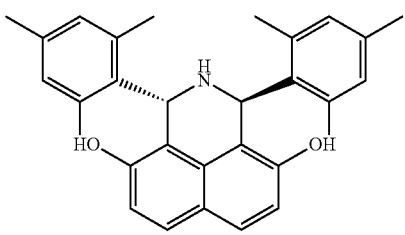

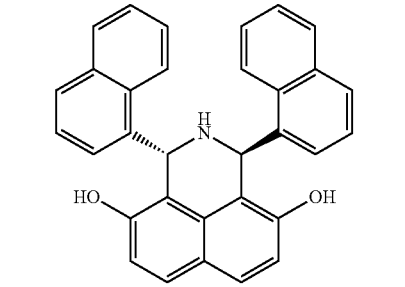

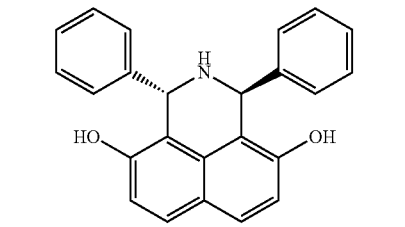

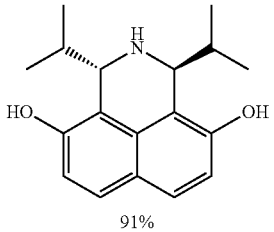

91%

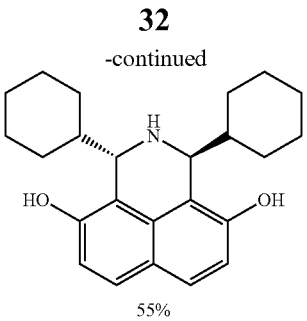

55%

Step B: Hydroxyl Activation

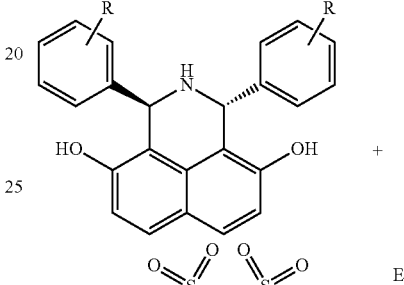

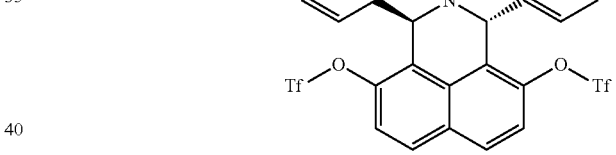

A stirred solution of 1 eq. of the cyclic diol (1 mmol) in 20 ml of dry DCM was cooled to 0° C. with an ice bath under argon. 6 eq. of $Et_3N$ (6 mmol) and 0.1 eq. of DMAP (0.1 mmol) were added into the stirred solution. A solution of 2.5 eq. of triflic anhydride (2.5 mmol) in 2 ml of dry DCM was added dropwise into the reaction mixture. After all the starting material was reacted (in about 30 min.) according to TLC (20% EtOAc in hexane) the reaction was quenched with water. The organic layer was extracted, washed with brine and dried over $Na_2SO_4$. The solvent was removed under vacuum. The crude product was purified by column chromatography on silica gel.

Structures of Representative Intermediates:

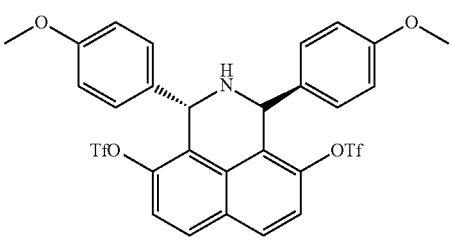

33
-continued

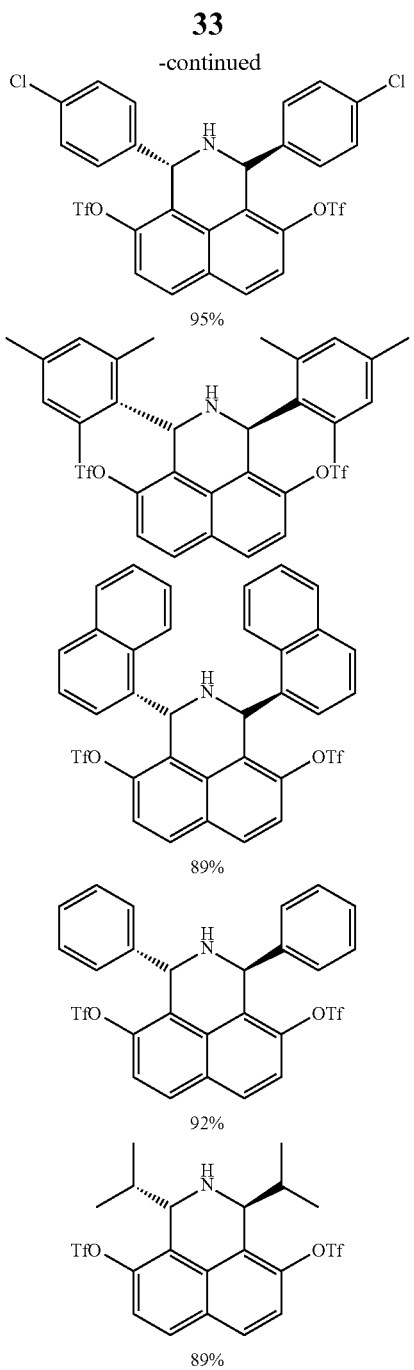

95%

89%

92%

89%

Step C: Stille Coupling

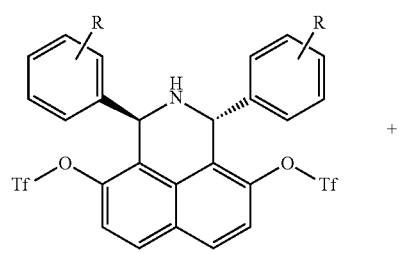

+

34
-continued

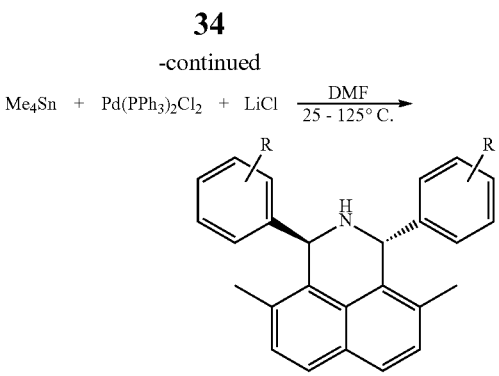

10 eq. of LiCl (2.6 mmol) were placed in a 10 ml 2 necked flask, dried with an heat gun under high vacuum and refilled with argon for 3 times. After LiCl was cooled to room temperature 2 ml of dry DMF were added, followed by 1 eq. of cyclic bistriflate (0.26 mmol)) and 3 eq. of $Me_4Sn$ (0.52 mmol). The mixture was stirred for 15 min. then 0.1 eq. of palladium catalyst were added (0.026 mmol). The reaction mixture was heated to 125° C. When all the starting material was reacted (and no mono product was left also) the heating was stopped and the reaction was quenched by adding water to the reaction mixture. The product was extracted with DCM and dried over $Na_2SO_4$. The solvent was removed under vacuum. The crude product was purified by column chromatography on silica gel.

Structures of Representative Amine Products:

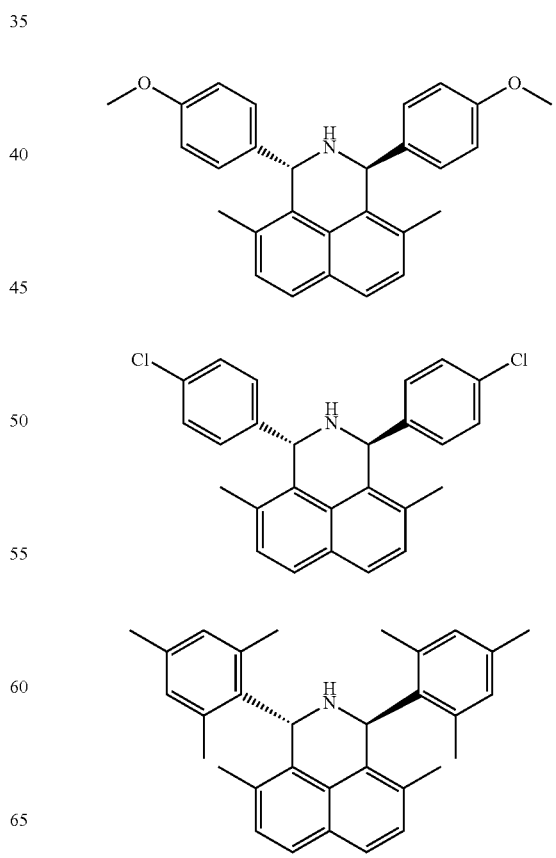

-continued

90%

93%

88%

In the next step, each of the amines is reacted with mCPBA in accordance with the procedure of Step 3, Example 1B, to give the corresponding nitroxyl compound:

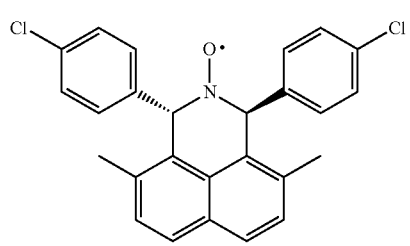
(3)

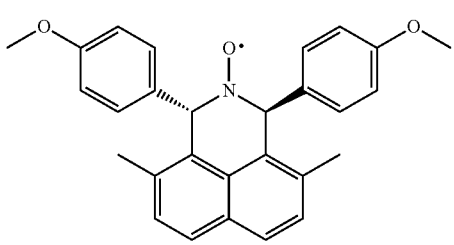
(2)

-continued

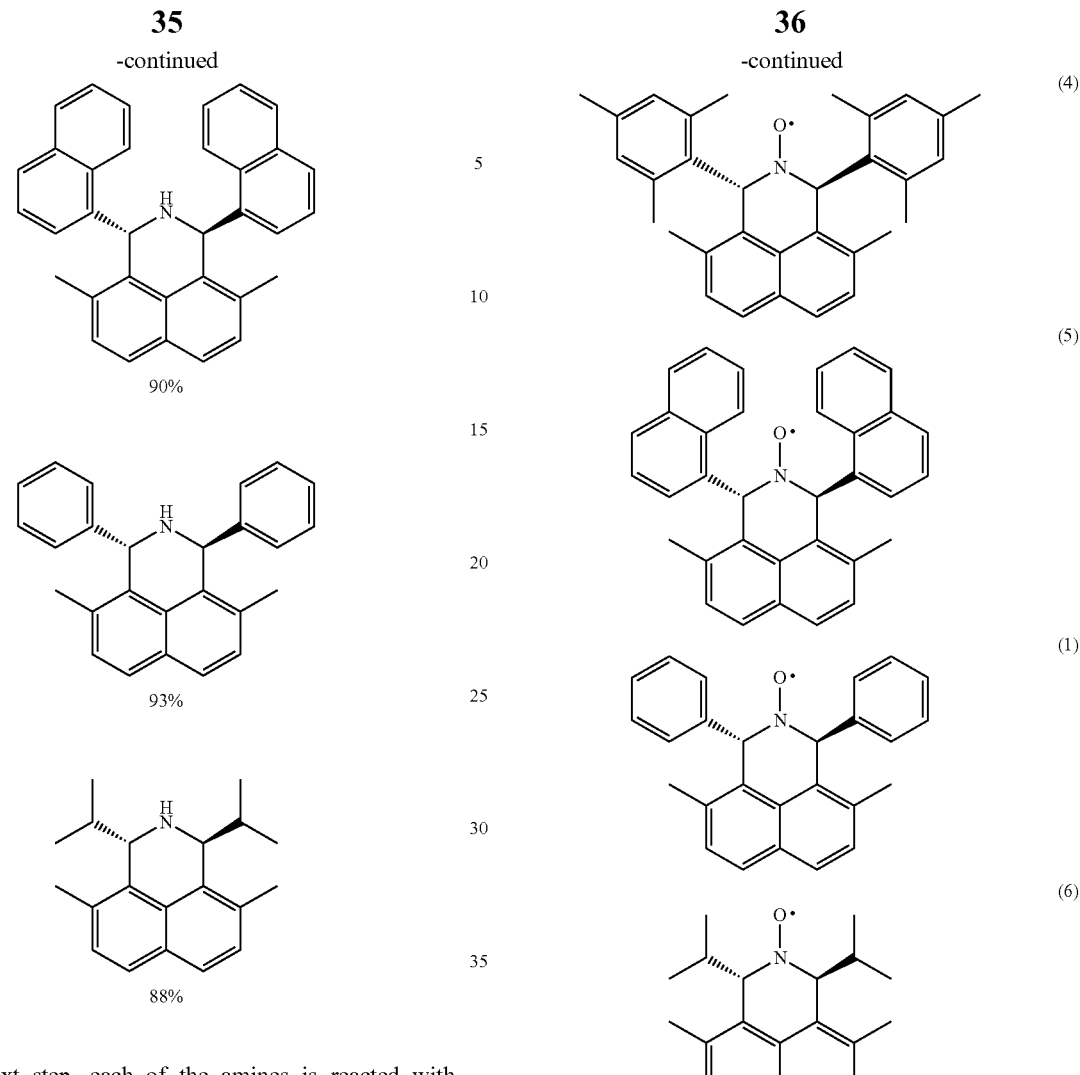
(4)

(5)

(1)

(6)

Enantiomeric Separation

In some experiments, the triflate bisphenyl compound obtained after step (B) underwent enantiomeric separation on HPLC column prior to Step (C). The following conditions were used for the separation:

Analytical Column:

Sample preparation: 2 mg of the bis triflate bisphenyl compound obtained from Step (B) were dissolved in 2 mL hexane.

Injection volume: 20 microliter.

The column used was an Amylose column (0.46 cm×25 cm), 100% Hexane eluent, 1 mL/min flow rate, Retention time 7.2 min and 9.2 min for the 1st and 2nd enantiomer, respectively.

Semipreparative Column 10 mg of the bistriflate bisphenyl compound obtained from Step (B) were dissolved in 2 mL hexane. The injection volume was 1 mL.

The column used was Lux 5u Amylose-2 New Column (250 mm×10.0 mm), 0.5% isopropanol/hexane eluent, 3 mL/min flow rate.

For the 1st enantiomer, the solvent fraction was collected between 6.0 min to 7.5 min, and for the 2nd enantiomer, the solvent fraction was collected between 8 min to 11 min.

After separation of the two enantiomers, all subsequent steps were conducted with enantiomerically pure compound.

Thus, Stille coupling was performed as described in Step (C) to get the enantiomerically pure bis methyl bis phenyl compound, which was then converted to the enantiomerically pure nitroxyl compound as described above.

Spectral Characterization

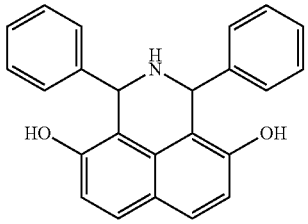 [SMILES: Oc1ccc2ccc(O)c3c2c1C(c1ccccc1)NC3c1ccccc1]

$^1$H NMR (400 MHz, CDCl$_3$) δ 7.99 (d, J=9.1 Hz, 2H), 7.49 (d, J=9.1 Hz, 2H), 7.30 (m, 6H), 7.07 (m, 4H), 5.55 (s, 2H).

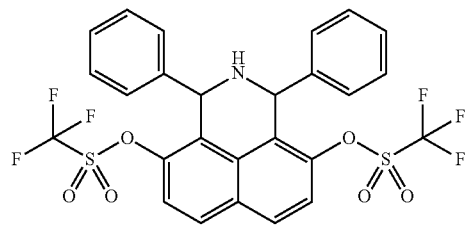 [SMILES: O=S(=O)(Oc1ccc2ccc(OS(=O)(=O)C(F)(F)F)c3c2c1C(c1ccccc1)NC3c1ccccc1)C(F)(F)F]

$^1$H NMR (400 MHz, CDCl$_3$) δ 8.00 (d, J=9.1 Hz, 2H), 7.51 (d, J=9.1 Hz, 2H), 7.32 (m, 6H), 7.09 (m, 4H), 5.57 (s, 2H).
$^{13}$C NMR (101 MHz, CDCl$_3$) δ=143.65, 140.53, 131.39, 131.15, 129.38, 128.87, 128.17, 128.03, 120.99, 54.86.

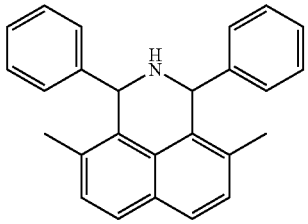 [SMILES: Cc1ccc2ccc(C)c3c2c1C(c1ccccc1)NC3c1ccccc1]

$^1$H NMR (400 MHz, Acetone) δ 7.74 (d, J=8.3 Hz, 2H), 7.24 (m, 8H), 7.07 (d, J=6.6 Hz, 4H), 5.36 (s, 2H), 1.99 (s, 6H).
$^{13}$C NMR (101 MHz, Acetone) δ=144.95, 133.78, 131.93, 131.59, 130.88, 129.18, 129.15, 127.62, 127.16, 57.57, 20.50.

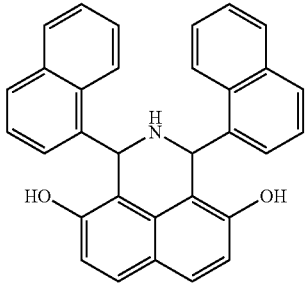 [SMILES: Oc1ccc2ccc(O)c3c2c1C(c1cccc2ccccc12)NC3c1cccc2ccccc12]

$^1$H NMR (400 MHz, DMSO) δ 9.06 (s, 2H), 7.95 (d, J=8.1 Hz, 2H), 7.80 (d, J=8.1 Hz, 2H), 7.66 (d, J=8.1 Hz, 2H), 7.60 (d, J=8.7 Hz, 2H), 7.33 (t, J=7.4 Hz, 2H), 7.14 (dd, J=14.6, 7.0 Hz, 4H), 6.85 (d, J=8.7 Hz, 2H), 6.67 (d, J=6.7 Hz, 2H), 5.81 (s, 2H).

$^{13}$C NMR (101 MHz, DMSO) δ=150.66, 139.90, 134.22, 133.28, 132.14, 128.80, 128.00, 127.48, 125.65, 125.50, 125.33, 125.19, 122.97, 116.08, 115.48.

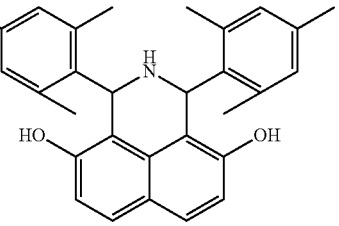

$^1$H NMR (400 MHz, CDCl$_3$) δ 7.62 (d, J=8.8 Hz, 2H), 6.92 (s, 2H), 6.86 (d, J=8.8 Hz, 2H), 6.80 (s, 2H), 5.80 (s, 2H), 4.89 (s, 2H), 2.32 (s, 6H), 2.27 (s, 6H), 1.83 (s, 6H).
$^{13}$C NMR (101 MHz, CDCl$_3$) δ=150.04, 138.53, 137.81, 134.13, 131.76, 131.64, 130.52, 128.29, 124.79, 116.50, 115.50, 51.00, 21.02, 20.96, 20.94.

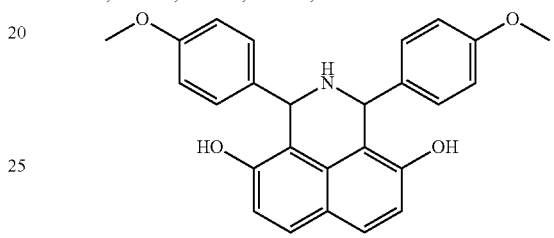

$^1$H NMR (400 MHz, DMSO) δ 9.01 (s, 2H), 7.49 (d, J=8.7 Hz, 2H), 6.93 (d, J=8.1 Hz, 4H), 6.79 (d, J=8.7 Hz, 2H), 6.72 (d, J=8.2 Hz, 4H), 5.07 (s, 2H), 3.64 (s, 6H).
$^{13}$C NMR (101 MHz, DMSO) δ=158.14, 150.40, 137.30, 132.27, 129.30, 127.52, 122.82, 116.93, 115.26, 113.56, 55.41, 53.21.

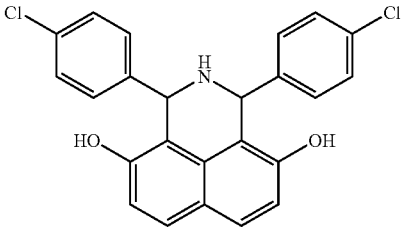 [SMILES: Oc1ccc2ccc(O)c3c2c1C(c1ccc(Cl)cc1)NC3c1ccc(Cl)cc1]

$^1$H NMR (400 MHz, DMSO) δ 9.15 (s, 2H), 7.46 (d, J=8.5 Hz, 2H), 7.15 (d, J=7.4 Hz, 4H), 7.00 (d, J=7.5 Hz, 4H), 6.76 (d, J=8.5 Hz, 2H), 5.06 (s, 2H).
$^{13}$C NMR (101 MHz, DMSO) δ=150.18, 143.70, 131.56, 130.71, 129.79, 127.72, 127.52, 122.37, 115.48, 114.87, 52.90.

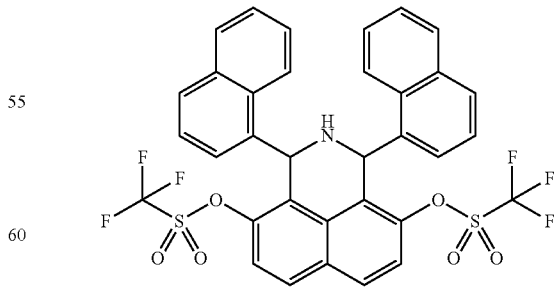

$^1$H NMR (400 MHz, CDCl$_3$) δ 8.04 (d, J=9.1 Hz, 2H), 7.88 (d, J=8.2 Hz, 2H), 7.81 (d, J=8.2 Hz, 4H), 7.52 (d, J=8.9 Hz, 2H), 7.45 (t, J=7.4 Hz, 2H), 7.25 (dd, J=16.9, 9.4 Hz, 4H), 6.72 (s, 2H), 6.25 (s, 2H).

$^{13}$C NMR (101 MHz, CDCl$_3$) δ=143.64, 135.16, 134.47, 131.52, 131.39, 129.51, 129.23, 129.02, 126.47, 125.92, 124.93, 123.69, 121.26, 119.93, 116.75, 52.24.

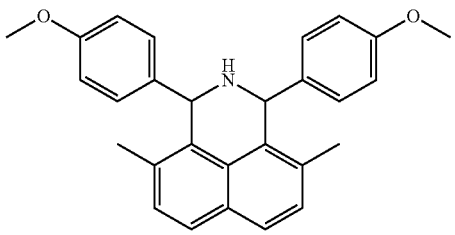

$^1$H NMR (400 MHz, CDCl$_3$) δ 7.69 (d, J=8.3 Hz, 2H), 7.20 (d, J=8.3 Hz, 2H), 6.98 (d, J=8.5 Hz, 4H), 6.78 (d, J=8.5 Hz, 4H), 5.31 (s, 2H), 3.77 (s, 6H), 2.02 (s, 6H).
$^{13}$C NMR (101 MHz, CDCl$_3$) δ=158.66, 135.90, 132.61, 131.25, 130.98, 129.90, 129.40, 128.57, 126.50, 114.00, 56.41, 55.35, 20.64.

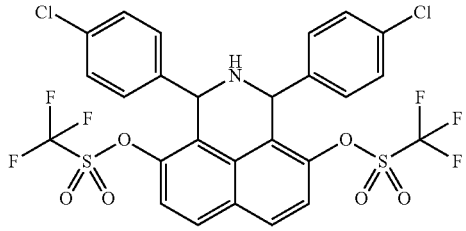 [SMILES: O=S(=O)(Oc1ccc2ccc(OS(=O)(=O)C(F)(F)F)c3c2c1C(c1ccc(Cl)cc1)NC3c1ccc(Cl)cc1)C(F)(F)F]

$^1$H NMR (400 MHz, CDCl$_3$) δ 8.00 (d, J=9.1 Hz, 2H), 7.49 (d, J=9.1 Hz, 2H), 7.27 (d, J=8.3 Hz, 4H), 7.00 (d, J=8.4 Hz, 4H), 5.50 (s, 2H).
$^{13}$C NMR (101 MHz, CDCl$_3$) δ=143.63, 138.86, 134.15, 131.45, 130.81, 129.76, 129.43, 129.13, 128.18, 121.12, 120.06, 116.88, 54.19.

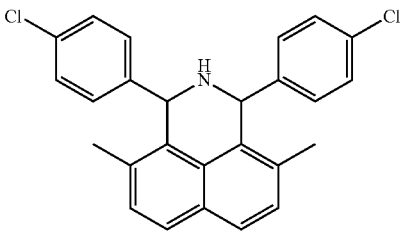 [SMILES: Cc1ccc2ccc(C)c3c2c1C(c1ccc(Cl)cc1)NC3c1ccc(Cl)cc1]

$^1$H NMR (400 MHz, CDCl$_3$) δ 7.72 (d, J=8.3 Hz, 2H), 7.23 (d, J=8.3 Hz, 6H), 7.00 (d, J=8.3 Hz, 4H), 5.30 (s, 2H), 2.01 (s, 6H).
$^{13}$C NMR (101 MHz, CDCl$_3$) δ=141.95, 132.99, 131.48, 131.42, 131.00, 128.91, 128.66, 126.90, 56.36, 20.60.

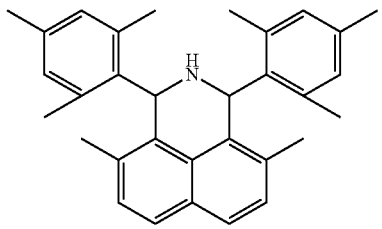

$^1$H NMR (400 MHz, CDCl$_3$) δ 7.65 (d, J=8.3 Hz, 2H), 7.17 (d, J=8.3 Hz, 2H), 6.90 (d, J=13.3 Hz, 2H), 6.67 (s, 2H), 5.74 (s, 2H), 2.30 (s, 6H), 2.25 (s, 6H), 1.97 (s, 6H), 1.43 (s, 6H).
$^{13}$C NMR (101 MHz, CDCl$_3$) δ=137.33, 137.12, 136.80, 136.22, 134.20, 131.32, 130.92, 130.85, 130.75, 129.83, 128.32, 126.27, 53.70, 20.96, 20.91, 20.86, 20.43.

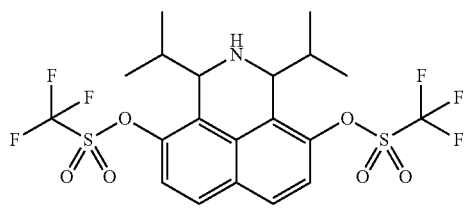 [SMILES: CC(C)C1NC(C(C)C)c2c(OS(=O)(=O)C(F)(F)F)ccc3ccc(OS(=O)(=O)C(F)(F)F)c1c23]

$^1$H NMR (400 MHz, CDCl$_3$) δ 7.80 (d, J=8.9 Hz, 2H), 7.41 (d, J=9.0 Hz, 2H), 4.43 (d, J=5.5 Hz, 2H), 2.36 (dd, J=13.3, 6.8 Hz, 2H), 0.96 (d, J=6.8 Hz, 6H), 0.79 (d, J=6.7 Hz, 6H).

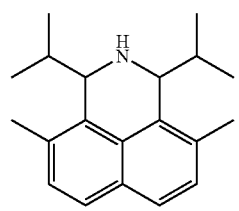 [SMILES: Cc1ccc2ccc(C)c3c2c1C(C(C)C)NC3C(C)C]

$^1$H NMR (400 MHz, CDCl$_3$) δ 7.51 (d, J=8.3 Hz, 2H), 7.17 (d, J=8.3 Hz, 2H), 4.29 (d, J=6.4 Hz, 2H), 2.44 (s, 6H), 2.18 (dq, J=13.4, 6.7 Hz, 2H), 0.88 (d, J=6.9 Hz, 6H), 0.71 (d, J=6.7 Hz, 6H).
$^{13}$C NMR (101 MHz, CDCl$_3$) δ=134.47, 130.50, 129.31, 129.29, 128.36, 125.08, 56.59, 31.37, 20.43, 20.36, 17.60.

Figure 4:
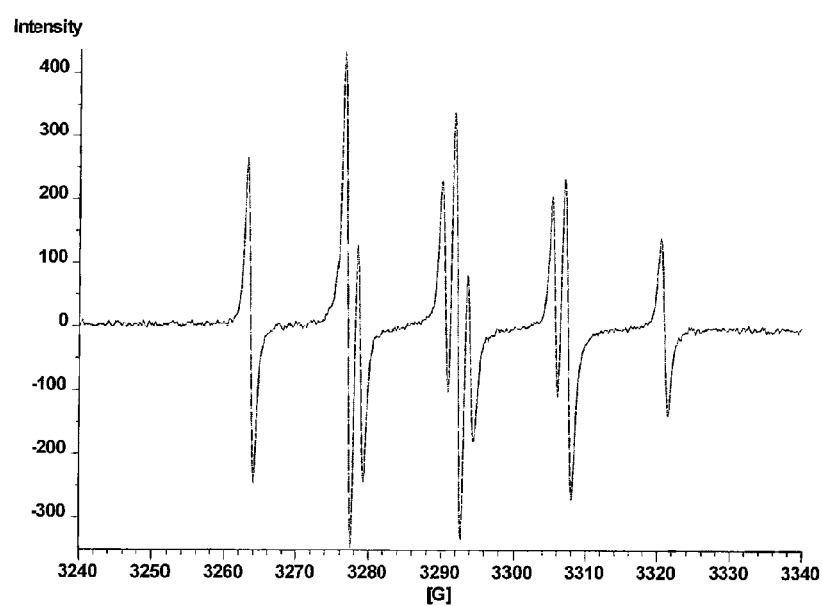
FIG. 4: ESR/EPR spectrum of nitroxyl catalyst 2 in toluene at room temperature.
Figure 5:
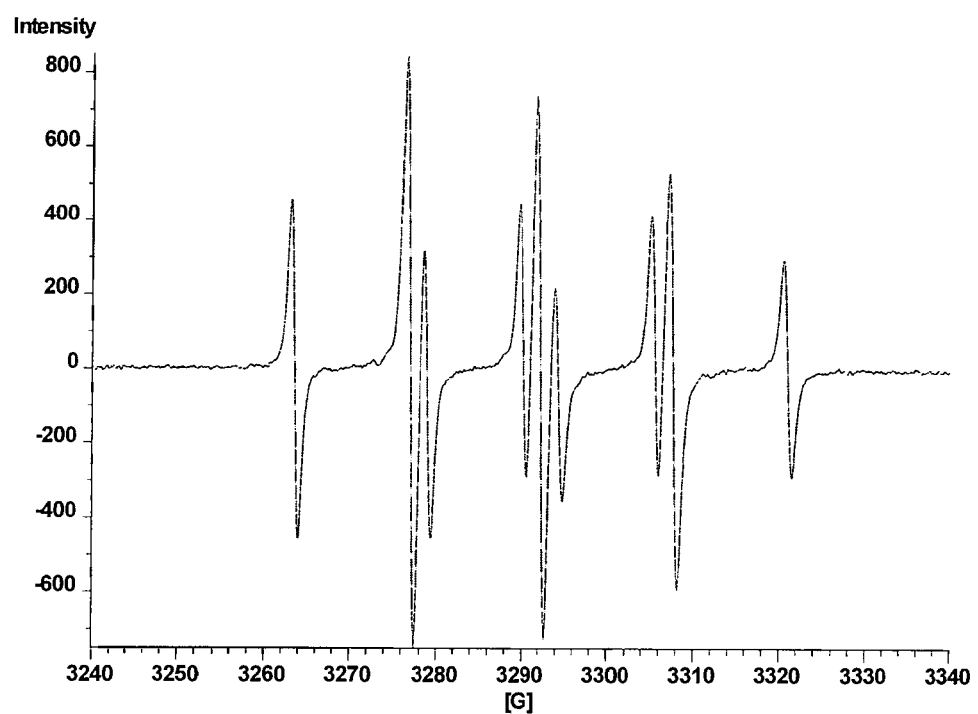
FIG. 5: ESR/EPR spectrum of nitroxyl catalyst 3 in toluene at room temperature.
Figure 6:
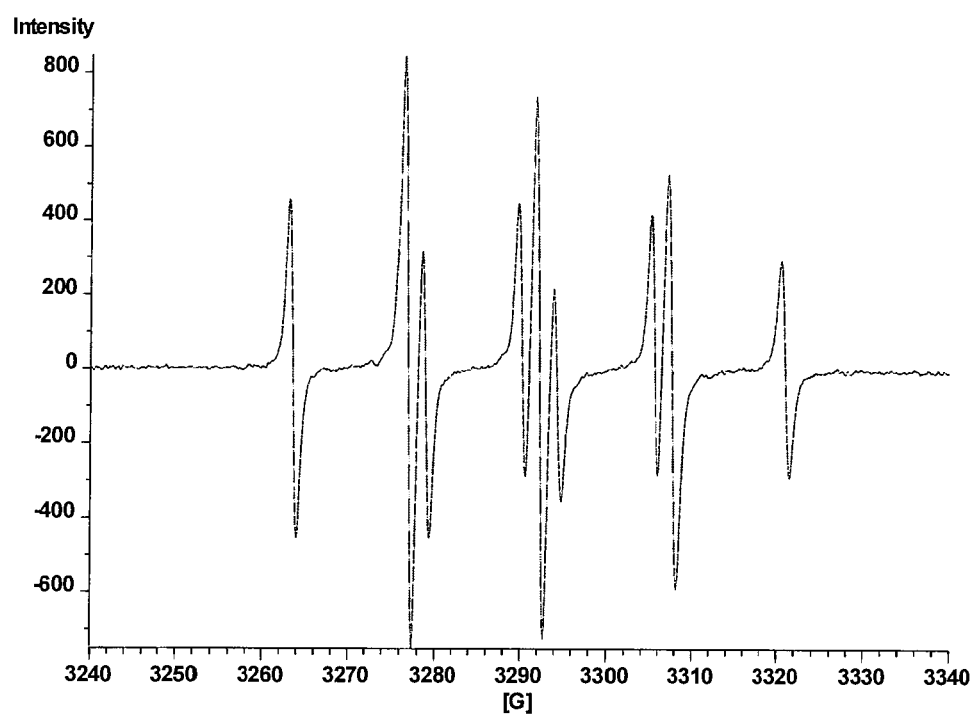
FIG. 6: ESR/EPR spectrum of nitroxyl catalyst 4 in toluene at room temperature.

The experimental room temperature ESR/EPR spectrum of the nitroxyl radical [2], [3] and [4] are shown in FIGS. 4, 5 and 6, respectively, using the same conditions described above for compound [1].

Example 6

Cyclic Asymmetric Amine Synthesis

This Example exemplifies the synthesis of asymmetric amines, which can be used as precursors for the preparation of compounds of Formula (I), or as ligands for transition metals, or as organocatalysts for, e.g., aldol reactions.

Step A: Synthesis of Asymmetrically Substituted Cyclic Azaphenalene

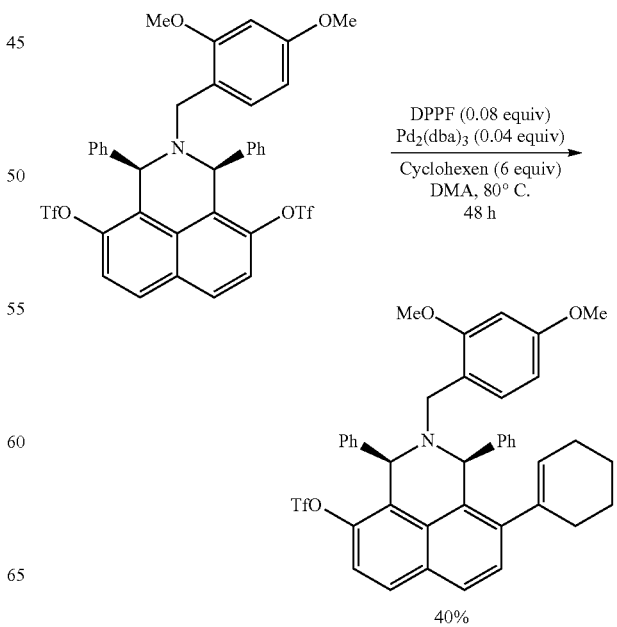

40%

Pd$_2$(dba)$_3$ (0.004 mmol) and dppf (0.008) were placed in 10 ml flask equipped with a stirring bar and the flask was evacuated and back filled with argon for 3 times. 1.2 ml of degassed DMA was added and the reaction mixture was stirred for 10 min at room temperature Bistriflate reagent (0.1 mmol), freshly distilled cyclohexene (0.6 mmol) and urotropine (0.4 mmol) were added to the reaction mixture which heated to reflux until full conversion of the triflate. The solvent was removed under vacuum and the crude was extracted from water to DCM. The solvent was evaporated and the product was purified by column chromatography on silica gel.

Step B: Hydrogenation

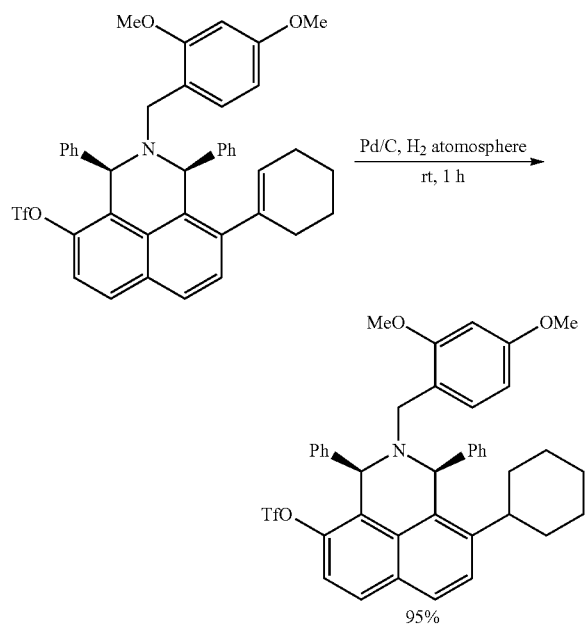

95%

Monotriflate protected amine (0.245 mmol) was dissolved in dry THF (5 ml). Pd/C (0.0245 mmol) was added to the reaction mixture under stirring. The reaction was done under hydrogen atmosphere until all starting material was reduced. The reaction mixture was transferred through a celite pad and the solvent was evaporated. The crude product was purified by column chromatography on silica gel.

Step C: Stille Coupling

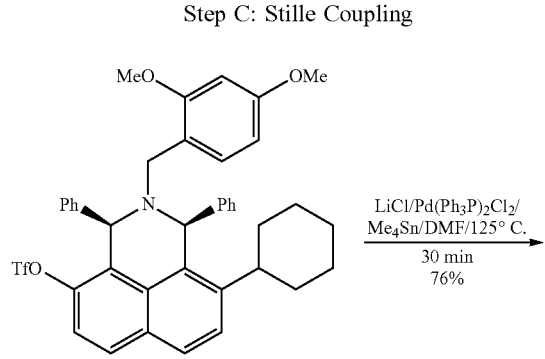

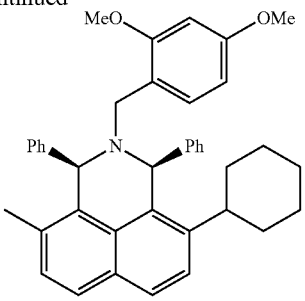

This step follows the steps of Example 5 Step C.

Step D: Deprotection

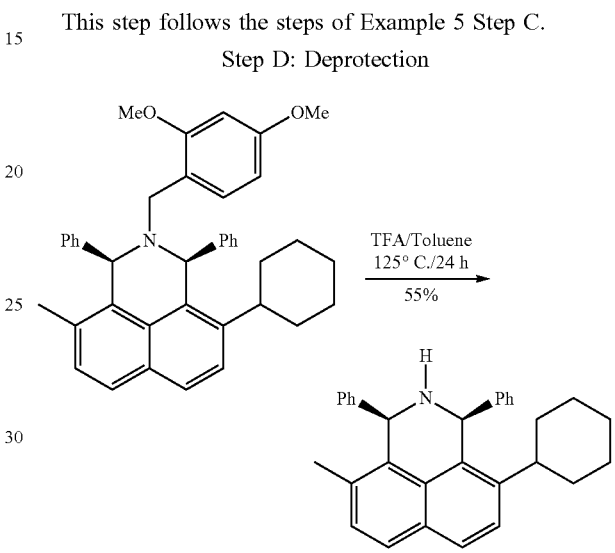

A 10 ml round flask was equipped with a condenser and a stirring bar. the starting material (0.7 mmol) was dissolved in 2 ml of TFA and 3 ml of toluene under nitrogen. The reaction mixture was heated to 120° C. and the reaction was stirred overnight. TLC (20% EtOAc in hexane) was held after mini-workup (extraction with sat. NaHCO$_3$) to see if no starting material was left. After all the starting material reacted, the reaction was cooled to room temperature and sat. NaHCO$_3$ was added during stirring. The reaction was extracted with DCM and dried over Na$_2$SO$_4$. The solvent was removed under vacuum. The crude product was purified by column chromatography on silica gel give the desired deprotected amine.

In the next step, the amine is reacted with mCPBA in accordance with the procedure of Step 3, Example 1B, to give the corresponding nitroxyl compound (7):

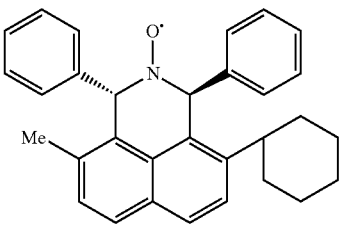

7

Example 7

Resolution of Racemic Menthol

A solution of 0.4 eq. of TCCA (232.41 mg, 1 mmol) in 2 ml of dry acetonitrile was prepared in a round 10 ml flask.

The mixture is stirred and cooled to 0° C. with an ice bath then 1 eq. (1 mmol) of racemic menthol was added to the solution. Freshly made enantiomerically pure catalyst prepared as described above (0.02 eq) was added to the stirred reaction mixture. The cooling was discontinued and the reaction mixture allowed to warm to room temperature. The reaction was followed closely by TLC and/or GC. After app. 50% conversion of the starting material was observed the reaction mixture was filtered through a piece of cotton. The solvent was removed under vacuum. The crude product was purified by column chromatography on silica gel to afford menthone and enantiomercially enriched menthol. NMR was identical to the published data.

Example 8

Use of Chiral Amine as a Catalyst for the Aldol Reaction of Propanal

Freshly distilled propanal (2 equiv, 2 mmol) was dissolved in dichlormethane. Enantiomerically pure amine catalyst (0.1 eq.) was added to the solution. The reaction was followed by TLC until all the aldehyde had been consumed. The reaction mixture was evaporated to dryness and purified by column chromatography on silica gel to afford (3S,4S)-4-hydroxy-3-methylhexan-2-one as the major product.

It is appreciated by persons skilled in the art that the present invention is not limited by what has been particularly shown and described hereinabove. Rather the scope of the present invention includes both combinations and subcombinations of various features described hereinabove as well as variations and modifications. Therefore, the invention is not to be constructed as restricted to the particularly described embodiments, and the scope and concept of the invention will be more readily understood by references to the claims, which follow.

What is claimed is:

1. A compound represented by the structure of formula I:

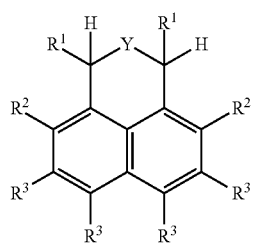

I including enantiomers, disasteromers, optically active, meso and racemic forms thereof, and salts thereof, wherein Y is

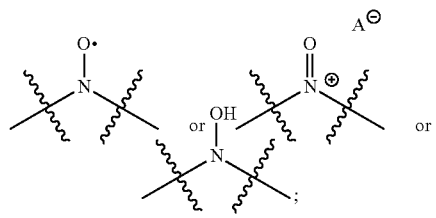

A is an anion;
$R^1$ is independently at each occurrence (i) phenyl, optionally substituted with one or more substituents selected from the group consisting of $C_1$-$C_6$ alkyl, $C_1$-$C_6$ alkoxy and halogen; (ii) naphthyl; or (iii) $C_1$-$C_6$ alkyl;
$R^2$ is independently at each occurrence a $C_1$-$C_6$ alkyl or a $C_3$-$C_8$ cycloalkyl; and
$R^3$ is H.

2. The compound according to claim 1, wherein the compound is represented by the structure of formula I-a:

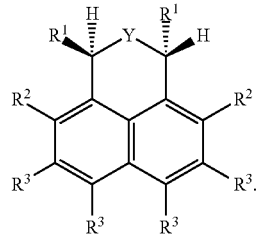

I-a

3. The compound according to claim 1, wherein the compound is selected from the group consisting of:
a nitroxyl derivative represented by the structure of formula II:

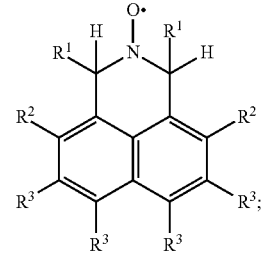

II an oxoammonium cation represented by the structure of formula III:

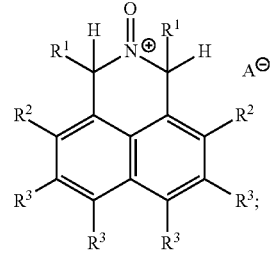

III a hydroxyamine derivative represented by the structure of formula IV:

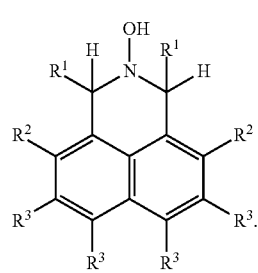

IV

4. The compound according to claim 3, wherein the compound is selected from the group consisting of:
a compound represented by the structure of formula II-a:

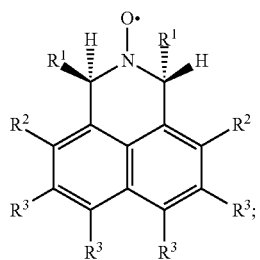

II-a a compound represented by the structure of formula III-a:

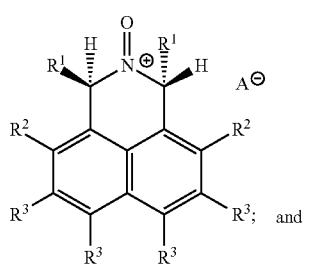

III-a and a compound represented by the structure of formula IVa:

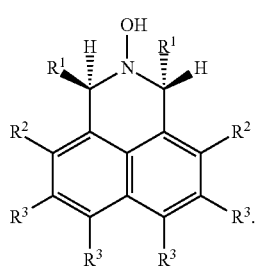

IV-a

5. The compound according to claim 1, wherein $R^1$ is selected from the group consisting of:
phenyl, 4-chlorophenyl, naphthyl, anisyl, mesityl and isopropyl.

6. The compound according to claim 1, wherein $R^2$ is selected from the group consisting of methyl and cyclohexyl.

7. The compound according to claim 1,
wherein $R^1$ is the same at each occurrence; or
wherein $R^2$ is the same at each occurrence; or
wherein $R^1$ is different at each occurrence; or
wherein $R^2$ is different at each occurrence; or
wherein $R^1$ and $R^2$ are the same; or
wherein $R^1$ and $R^2$ are different from each other.

8. The compound according to claim 1, which is selected from the group consisting of:

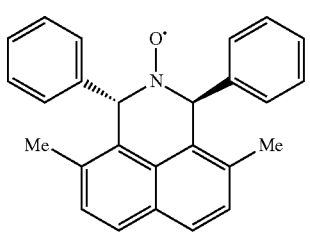

1

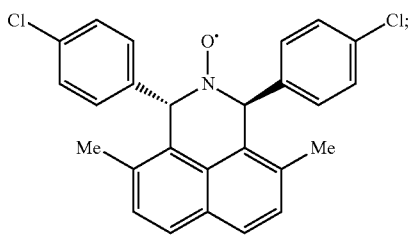

2

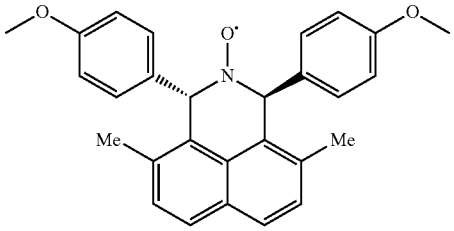

3

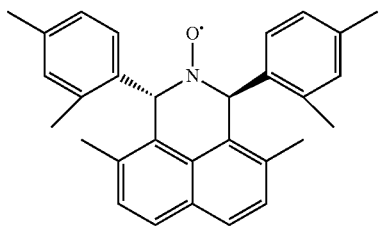

4

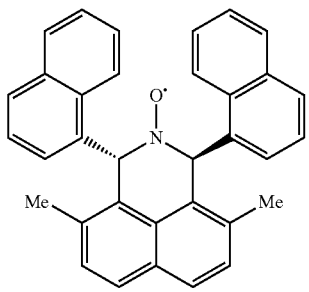

5

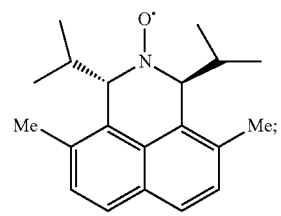

6

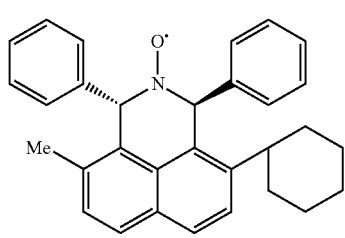

7 and hydroxylamine or oxoammonium derivatives of any of the foregoing.

9. The compound according to claim 1, which is in a racemic form or in optically active form.

10. An amine derivative represented by the structure of formula V:

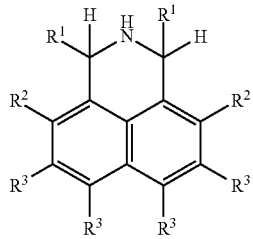

V wherein
- $R^1$ is independently at each occurrence (i) phenyl, optionally substituted with one or more substituents selected from the group consisting of $C_1$-$C_6$ alkyl, $C_1$-$C_6$ alkoxy and halogen; (ii) naphthyl; or (iii) $C_1$-$C_6$ alkyl;
- $R^2$ is independently at each occurrence a $C_1$-$C_6$ alkyl or a $C_3$-$C_5$ cycloalkyl; and
- $R^3$ is H.

11. The amine derivative according to claim 10, which is selected from the group consisting of:

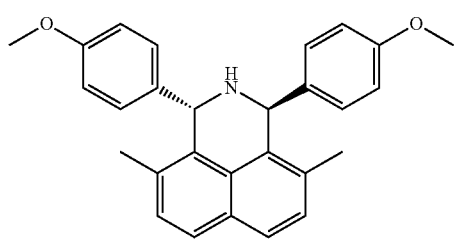

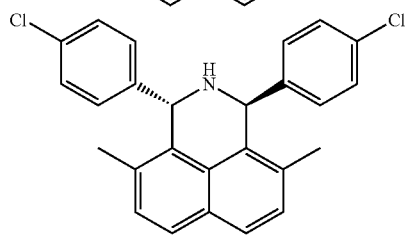

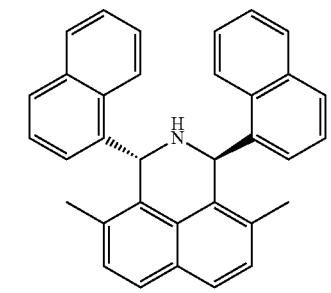

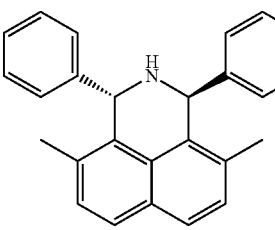

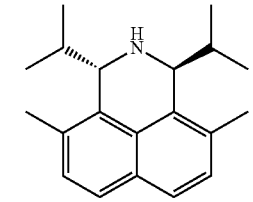

and

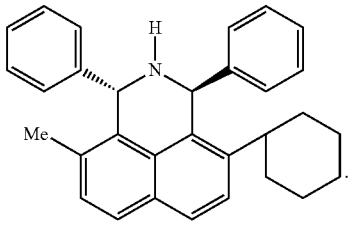

* * * * *